（12）United States Patent
Sanders et al.

(10) Patent No.: US 9,539,075 B2
(45) Date of Patent: Jan. 10, 2017

(54) DEVICES, SYSTEMS AND METHODS FOR THE WHITENING OF TEETH

(75) Inventors: Daniel Sanders, West Orange, NJ (US); Ben Zion Spector, Tel Mond (IL)

(73) Assignee: MAVRIK DENTAL SYSTEMS, LTD., Ra'anana (IL)

( * ) Notice: Subject to any disclaimer, the term of this patent is extended or adjusted under 35 U.S.C. 154(b) by 195 days.

(21) Appl. No.: 14/241,973

(22) PCT Filed: Sep. 12, 2012

(86) PCT No.: PCT/US2012/054652
§ 371 (c)(1),
(2), (4) Date: Feb. 28, 2014

(87) PCT Pub. No.: WO2013/039906
PCT Pub. Date: Mar. 21, 2013

(65) Prior Publication Data
US 2014/0227657 A1    Aug. 14, 2014

Related U.S. Application Data

(60) Provisional application No. 61/533,303, filed on Sep. 12, 2011, provisional application No. 61/596,238, filed on Feb. 8, 2012.

(51) Int. Cl.
*A61C 19/00* (2006.01)
*A61C 19/06* (2006.01)

(52) U.S. Cl.
CPC .................................. *A61C 19/066* (2013.01)

(58) Field of Classification Search
CPC .......... A61C 17/00; A61C 17/02; A61C 17/24
(Continued)

(56) References Cited

U.S. PATENT DOCUMENTS 2,258,883 A    10/1941  Cressler
2,937,445 A     5/1960  Erickson
(Continued)

FOREIGN PATENT DOCUMENTS

WO    2004/069215 A2    8/2004
WO    2005/094768 A1   10/2005
(Continued)

OTHER PUBLICATIONS

International Search Report and Written Opinion, PCT/US2012/054652, dated Nov. 13, 2012.
(Continued)

*Primary Examiner* — Ralph Lewis
(74) *Attorney, Agent, or Firm* — The Dobrusin Law Firm, P.C.

(57) ABSTRACT

A device, method, and system are provided for aiding the whitening of teeth. The device includes a mouthpiece suitable for implementing a dental treatment, wherein the mouthpiece includes one or more stock dental cover layers suitable for forming a treatment cavity having a vacuum, wherein the dental cover layers includes a layer over the upper teeth and/or a layer over the lower teeth; and one or more treatment supply layers wherein the treatment supply layer has one or more flow channel in fluid communication with the treatment cavity so that the treatment supply layer can deliver and/or remove one or more treatment fluids from the treatment cavity.

26 Claims, 14 Drawing Sheets

(58) Field of Classification Search
USPC .......................................... 433/80, 215, 216
See application file for complete search history.

(56) References Cited

U.S. PATENT DOCUMENTS

| | | | |
|---|---|---|---|
| 2,957,476 A | 10/1960 | Freeman | |
| 3,049,806 A | 8/1962 | Cofresi | |
| 3,481,329 A | 12/1969 | Warren | |
| 3,489,141 A * | 1/1970 | Warren, Jr. | A61C 17/0211 |
| | | | 15/345 |
| 3,527,218 A | 9/1970 | Westine | |
| 3,527,219 A | 9/1970 | Greenberg | |
| 3,536,069 A | 10/1970 | Gores | |
| 3,566,869 A | 3/1971 | Crowson | |
| 3,669,101 A | 6/1972 | Kleiner | |
| 3,731,675 A * | 5/1973 | Kelly | A61C 17/0211 |
| | | | 601/164 |
| 3,742,942 A | 7/1973 | Westline | |
| 3,772,790 A | 11/1973 | Swan-Gett et al. | |
| 3,840,992 A | 10/1974 | English | |
| 4,059,101 A | 11/1977 | Richmond | |
| 4,106,501 A | 8/1978 | Ozbey et al. | |
| 4,138,814 A | 2/1979 | Weitzman | |
| 4,164,940 A | 8/1979 | Quinby | |
| 4,192,071 A | 3/1980 | Erickson | |
| 4,560,351 A * | 12/1985 | Osborne | A61C 19/08 |
| | | | 433/215 |
| 4,983,381 A | 1/1991 | Zaragoza | |
| 4,993,947 A | 2/1991 | Grosrey | |
| 5,078,604 A * | 1/1992 | Malmin | A61C 5/122 |
| | | | 433/136 |
| 5,104,315 A | 4/1992 | McKinley | |
| 5,365,624 A | 11/1994 | Berns | |
| 5,443,386 A * | 8/1995 | Viskup | A61C 17/0211 |
| | | | 433/216 |
| 5,487,662 A | 1/1996 | Kipke et al. | |
| 5,513,986 A | 5/1996 | Feltham et al. | |
| 5,575,654 A | 11/1996 | Fontenot | |
| 5,682,904 A | 11/1997 | Stinnett | |
| 6,077,073 A | 6/2000 | Jacob | |
| 6,152,733 A | 11/2000 | Hegemann et al. | |
| 6,162,055 A | 12/2000 | Montgomery et al. | |
| 6,254,391 B1 | 7/2001 | Darnell | |
| 6,340,301 B2 | 1/2002 | Darnell | |
| 6,343,932 B1 | 2/2002 | Wiesel | |
| 6,364,665 B1 | 4/2002 | Trettenero | |
| 6,391,283 B1 | 5/2002 | Jensen et al. | |
| 6,439,889 B1 | 8/2002 | Chen et al. | |
| 6,616,447 B1 | 9/2003 | Rizoiu | |
| 6,685,923 B2 | 2/2004 | Peterson et al. | |
| 6,689,344 B2 | 2/2004 | Chang et al. | |
| 6,746,679 B2 | 6/2004 | Nathoo | |
| 6,770,266 B2 | 8/2004 | Santarpia, III et al. | |
| 6,893,259 B1 * | 5/2005 | Reizenson | A61C 17/0211 |
| | | | 433/29 |
| 6,981,874 B2 | 1/2006 | Allred et al. | |
| 7,118,377 B2 | 10/2006 | Inoue et al. | |
| 7,189,385 B2 | 3/2007 | Montgomery | |
| D543,280 S | 5/2007 | Khubani | |
| 7,331,784 B2 | 2/2008 | Suzuki | |
| 7,572,124 B2 | 8/2009 | Cipolla et al. | |
| 7,601,002 B2 | 10/2009 | Milanovich et al. | |
| 7,748,070 B2 | 7/2010 | Chan et al. | |
| 7,758,621 B2 | 7/2010 | Altshuler et al. | |
| 7,763,016 B2 | 7/2010 | Altshuler et al. | |
| 7,775,795 B2 | 8/2010 | Khawaled et al. | |
| 7,845,039 B2 | 12/2010 | Chan et al. | |
| 7,935,107 B2 | 5/2011 | Altshuler et al. | |
| 7,942,915 B2 | 5/2011 | Altshuler et al. | |
| 7,942,916 B2 | 5/2011 | Altshuler et al. | |
| 8,002,768 B1 | 8/2011 | Altshuler et al. | |
| 8,007,277 B2 | 8/2011 | Fischer et al. | |
| 8,029,278 B1 | 10/2011 | Levine | |
| 8,109,924 B2 | 2/2012 | Altshuler et al. | |
| 8,182,473 B2 | 5/2012 | Altshuler et al. | |
| 8,205,618 B2 | 6/2012 | Berghash et al. | |
| 8,215,954 B2 | 7/2012 | Levine | |
| 8,277,215 B2 | 10/2012 | McLean et al. | |
| 2001/0012608 A1 | 8/2001 | Darnell | |
| 2001/0038997 A1 | 11/2001 | Lindquist | |
| 2002/0110780 A1 | 8/2002 | Zegarelli | |
| 2002/0137001 A1 | 9/2002 | Cipolla et al. | |
| 2003/0104341 A1 | 6/2003 | Zavitsanos et al. | |
| 2004/0185013 A1 | 9/2004 | Burgio et al. | |
| 2005/0037315 A1 | 2/2005 | Inoue et al. | |
| 2005/0196725 A1 | 9/2005 | Fu | |
| 2005/0214720 A1 | 9/2005 | Milanovich et al. | |
| 2007/0015112 A1 | 1/2007 | Hochman et al. | |
| 2007/0184404 A1 | 8/2007 | Johnki | |
| 2008/0063612 A1 | 3/2008 | MacDonald et al. | |
| 2009/0123886 A1 | 5/2009 | Vaska | |
| 2011/0027746 A1 | 2/2011 | McDonough et al. | |
| 2011/0076636 A1 | 3/2011 | Wolff et al. | |
| 2011/0104633 A1 | 5/2011 | Levine | |
| 2011/0185525 A1 | 8/2011 | Stapelbroek et al. | |
| 2011/0189626 A1 | 8/2011 | Sanzari | |
| 2011/0289709 A1 | 12/2011 | Attaway | |
| 2012/0156648 A1 | 6/2012 | Kaufman et al. | |

FOREIGN PATENT DOCUMENTS

| | | |
|---|---|---|
| WO | 2006/073559 A1 | 7/2006 |
| WO | 2007/117926 A3 | 10/2007 |

OTHER PUBLICATIONS

International Preliminary Report on Patentability, PCT/US2012/054652, dated Mar. 12, 2014.
Goldberg et al, "Tooth Bleaching Treatments", L'eelaireissement dentaire—evaluation des therapeutiques, 2005 Association Dentaire Francaise, Paris. pp. 1-50; www.ppgmea.com/docs/tooth/20.pdf.
Office Action from the United Kingdom Patent Office, Copending Application No. GB1400767.8 dated Aug. 6, 2014.
Office Action from the Eurasian Patent Office, Copending Application No. 201490628/31 dated Feb. 12, 2016.

\* cited by examiner

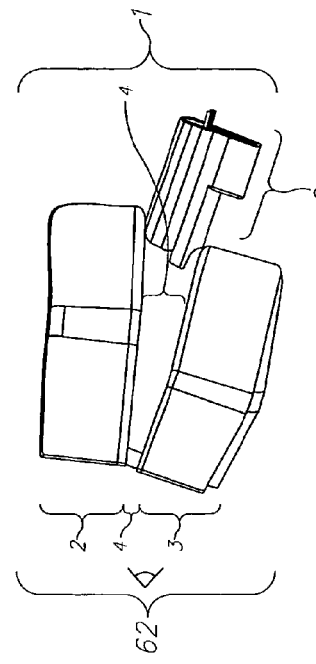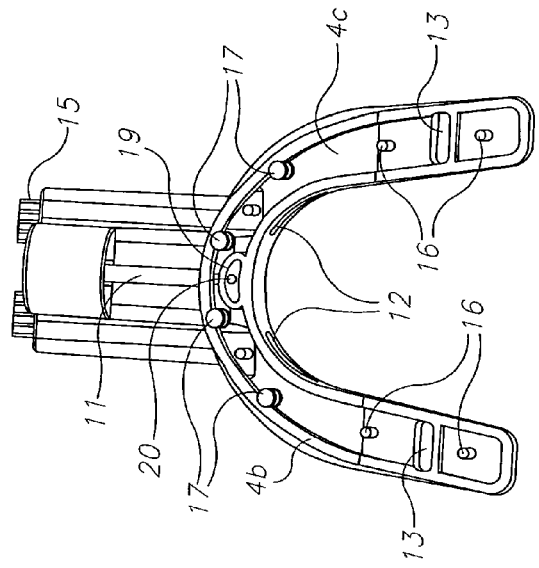

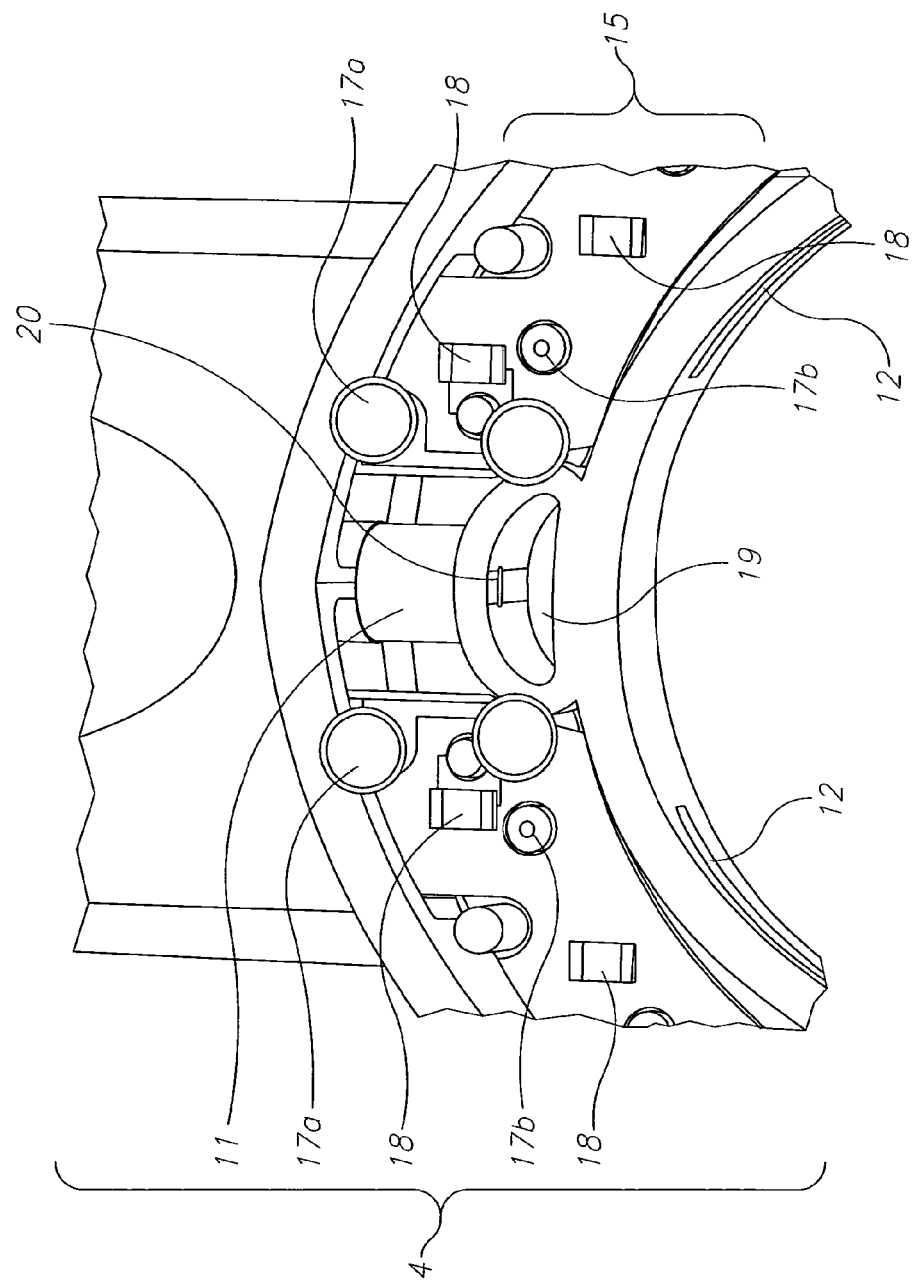

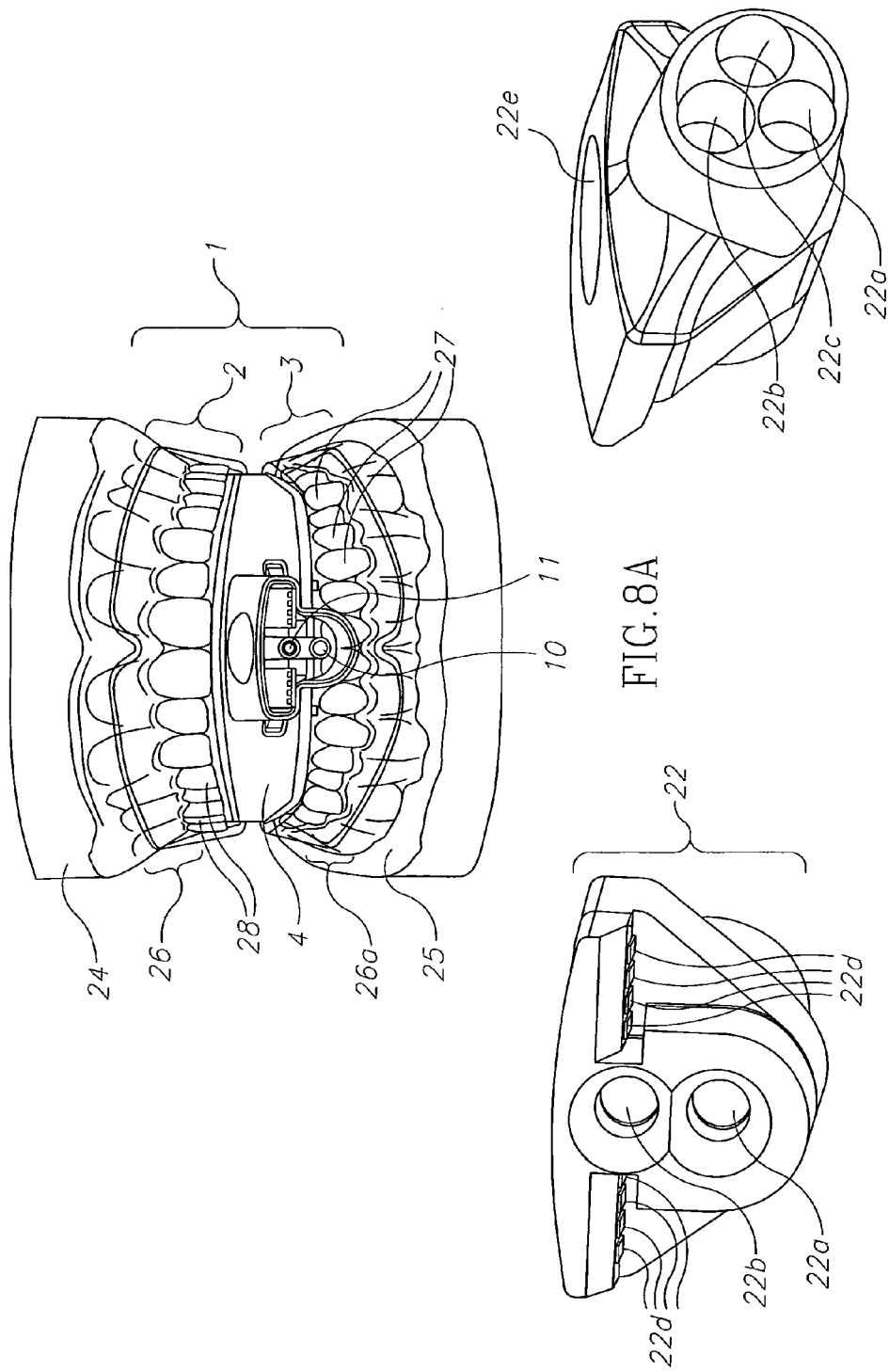

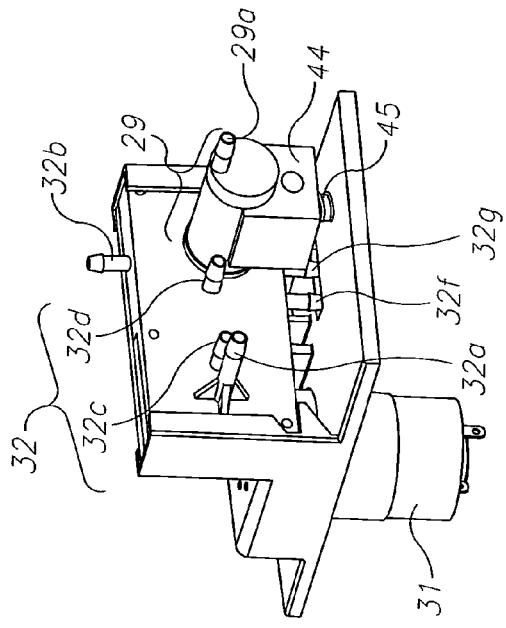
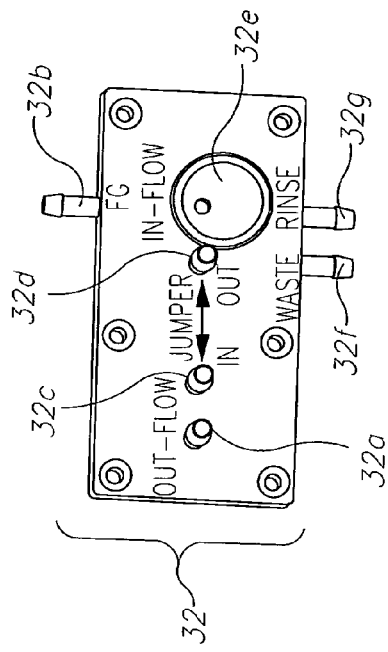
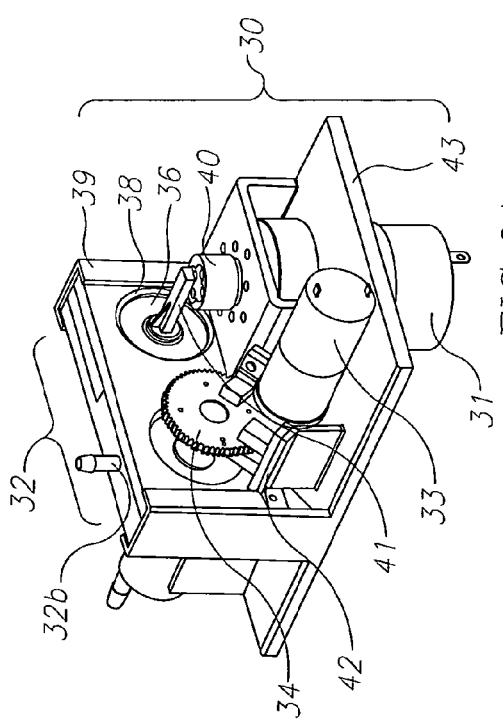
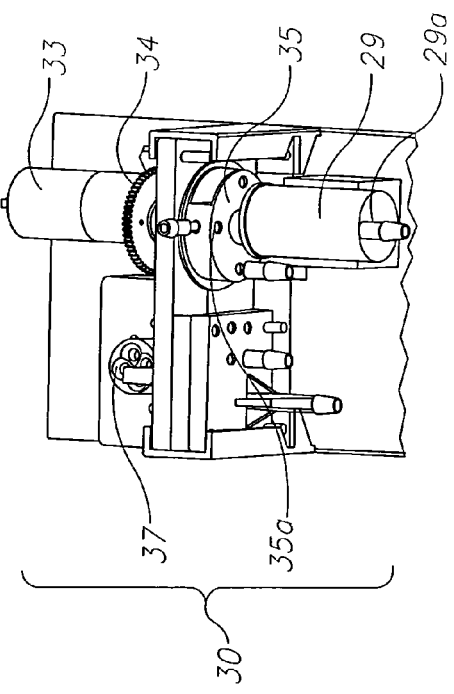

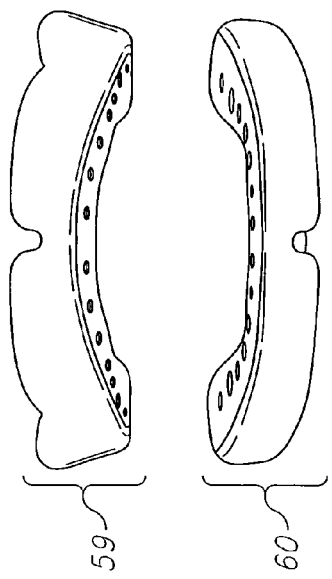
FIG.13A
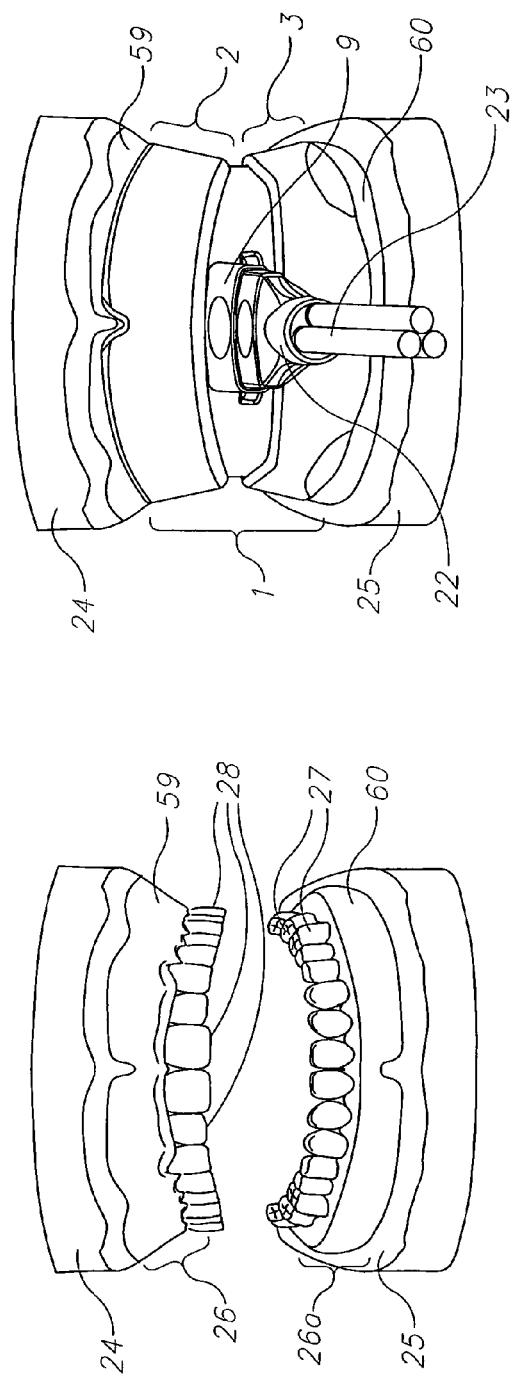
FIG.13B
FIG.13C

DEVICES, SYSTEMS AND METHODS FOR THE WHITENING OF TEETH

CLAIM OF PRIORITY

This application claims priority to U.S. Provisional Patent Application No. 61/533,303, filed Sep. 12, 2011, entitled "Devices, Methods and Systems for the Whitening of Teeth", and from U.S. Provisional Patent Application No. 61/596,238, filed Feb. 8, 2012, entitled "Devices, Methods and Systems for the Whitening of Teeth", which were filed by the same inventor, and are incorporated in their entirety herein by reference.

FIELD OF THE INVENTION

The device and method of the present invention relates to dental treatments and more specifically, to teeth whitening treatments.

BACKGROUND OF THE INVENTION

There is a wide variation in the visual color shade values of the teeth. There is also commonly found a wide variation within the same individual of the different teeth in the mouth, due to a variety of natural factors. Often, in the same individual for example, the natural color shade of the upper and lower canines are more "yellow" than the upper and lower central and lateral incisors and it is common to find that the upper (maxillary) teeth are generally "whiter" than the lower (mandibular) teeth. It is often also common to find that the anterior teeth are in general "whiter" than the posterior teeth. Known dental whitening treatments that will be described below do not appear to take into account any of these significant variations in baseline (pre-treatment) color shades which are normally present in the same individual patient prior to treatment. This means that whatever whitening result that is obtained using the various whitening techniques currently in use cannot in general be customized to a given patient's needs based on the initial differing baseline color shades values of the teeth that the patient presented with prior to treatment. It is therefore extremely unlikely to obtain a completely uniform final whitening result utilizing the current systems in use.

There are numerous over-the-counter consumer "whitening" products such as toothpastes, whitening strips and mouthwashes. These will not be discussed further.

The standard professional dental treatment for whitening teeth is to provide the user either by way of the dental office some form of dental tray appliance (custom made from dental molds taken from each patient and made to fit to each patient) and mild concentrations of a whitening agent for self-application at home. These treatments are commonly referred to as the "home" whitening method.

The anatomical area posterior to the terminal teeth on the right and left sides of either the upper and lower jaws is referred to as the retro-molar pad. The dental tray appliance is typically fabricated to cover these terminal teeth and their terminal borders are the retro-molar pads. There is significant variability between patients as to the size of their teeth, and the shape of their dental arches. In regards to fabricating a tray to properly cover all the teeth contained within any given arch, the variable width and length of the dental arch must be considered.

The user is instructed to fill the full arch dental tray with the mild whitening chemical agent (gel) and place the tray on the teeth for up to several hours each day over the course of a minimum of one to two weeks. The custom dental trays cover all the teeth either in the upper or lower jaw. This means that the user can whiten both the front and back teeth with this treatment method using one tray for the upper teeth and one tray for the lower teeth. This teeth whitening technique is referred to as a "compression" technique, as the whitening agent is mainly contained during treatment within the closed confines of the tray and not left exposed to the atmosphere.

It has been demonstrated that the use of a compression technique with whitening agents potentiates whitening as this encourages oxygen ions release by the whitening agent (the primary means of whitening the teeth) to migrate towards the inside of the enamel structure of the teeth rather than to be released into the surrounding air (Miara and Miara, 2003).

It has been demonstrated that the natural saliva in the oral cavity contains a peroxidase enzyme which naturally breaks down and neutralizes hydrogen peroxide (Tenovuo and Pruitt, 1984). Utilizing custom made professional whitening trays which adapt to the teeth more closely than over the counter stock whitening trays reduces the amount of saliva that can seep into the trays and come in contact with the active hydrogen peroxide that has been placed into the trays. This reduces the amount of deactivation or breakdown by the saliva of the active gel and so increases the chemical whitening effect of this professional whitening treatment in comparison to over the counter "stock" whitening trays (which are not as well adapted to the teeth and so allow a significant amount of saliva to leak into these trays).

The custom "whitening" dental tray appliance(s) of the "home" treatment method mentioned above requires two dental visits. During the first office visit, dental impressions of the dental arches are taken in the dental office from which are fabricated custom-fitted rigid or semi-rigid thin plastic "whitening" tray(s). These trays outer limiting surfaces can either be closely contoured to the teeth or made significantly larger than the teeth. The above "home" treatment method requires the user to devote considerable time (as mentioned above) to achieve a moderate degree of teeth whitening, and due to the excessive exposure time of the teeth and gums to the whitening agents can often cause the teeth to become sensitive as well as irritating or chemically burning the gum and oral mucosal tissues of the mouth. Many patients find the effort required to achieve a sufficiently "whiter teeth" result too taxing, and there is often a very high rate of non-compliance, resulting in a poor final whitening result of the teeth.

These obvious drawbacks in the professional "home" whitening treatment method has in recent years given rise to professional dental treatments referred to in the dental field as "in office" or "power whitening" treatment. This treatment method involves applying in the dental office, utilizing and under the supervision of professional dental staff, more highly concentrated (and more caustic) formulations of various teeth whitening chemical agents than were previously used for the "home" whitening treatments. This "power" teeth whitening technique typically takes around one hour treatment time. To protect the gingival tissues from these highly concentrated whitening agents, a "paint-on dam" or protective coating (a layer of material applied in a strip at the gum line which is placed in a scalloped shape to contour to the gum-line) is applied by hand (very time-consuming) and hardened with a standard dental UV light. Additionally, an uncomfortable lip and cheek retractor device is inserted into the mouth along with cotton rolls (and gauze as needed) in order to try and protect the rest of the oral tissues of the mouth from these highly concentrated and caustic whitening agents.

These precautions are necessary, as contact of these highly concentrated chemical whitening agents used in the "power" whitening with the above mentioned soft tissues of the mouth will, in a few seconds, cause significant chemical burning and pain to the patient. Typically, three applications of the whitening agent (for approximately 20 minutes each) limited to only the buccal (front) surfaces of only the anterior teeth are made, wherein the previous application is washed and suctioned off the teeth and replaced with the next application. The lingual (inner) surfaces of these anterior teeth and the posterior teeth in their entirety are not "whitened" using this technique. The "power" whitening technique does not utilize a tray device of any kind. The whitening agent is applied in an open "non-compressed" paint-on manner onto the external buccal surfaces of the limited teeth to be treated and so does not have the whitening advantages of the compression effect of the whitening gel using trays as described previously (home whitening technique).

Over the past two decades there has also been a shift in "in office" or "power whitening" treatments to utilize "light activated" whitening agents over the older whitening agents that did not require light activation to potentiate an oxidation (whitening) chemical reaction. These newer light activated whitening agents are chemically formulated to oxidize when exposed to a concentrated intense light source which acts as a catalyst to potentiate the chemical oxidation of these whitening agents.

There is much controversy in the dental field as to whether the use of light activation of the whitening gels enhances the chemical whitening effect of these gels. It has been postulated that it is actually the heat generated by the light and not any specific wavelength of the light that actually increases the chemical activity and hence the whitening activity of these whitening gels.

The light emitting devices currently being used in the dental field can, in general, only reach the anterior portion of the mouth and only after the lips and cheeks have been retracted using devices as were described above. This is due to the limited natural elasticity of the lips and muscles surrounding the mouth which limit the number of teeth that can comfortably and safely retracted and exposed to the light source and the highly concentrated "power" whitening chemical agents while still protecting the soft tissues of the oral cavity from these highly caustic whitening agents.

As mentioned above, these limitations typically result in "power whitening" treatments of, at a maximum, the front upper 10 and front lower 10 teeth, (the upper and lower central and lateral incisors, canines and first and second bicuspids) for a maximum treatment of 20 teeth (there are typically 28-32 teeth in the human mouth). Due to the limitations already mentioned, it is common practice to find that only the top 8 and bottom 8 front teeth are "power" whitened for a total of 16 (only 50%) of the teeth often present in the patient's mouth, a distinct disadvantage of this teeth whitening technique.

A further limitation of the treatment area is that in general the lights used in the "power" whitening can be positioned by the operator into the patient's mouth to illuminate mainly the buccal (front or outer) surfaces of the anterior teeth while only poorly illuminating the lingual (back or inner) surfaces of these front teeth. It is also extremely difficult for the dental practitioner to apply the "paint-on dam" protective coating at the gum-line of the lingual "inner" surfaces of the anterior teeth and almost impossible for the dentist to isolate the very active tongue with the current isolation devices and materials available in the dental field. This means that these sensitive oral tissues are extremely difficult to isolate from the caustic chemical burning of the highly concentrated "power" whitening agents.

The above explains why whitening of the inner (lingual) surfaces of the anterior teeth are rarely done in this technique and the posterior teeth are never whitened at all with this technique. Moreover, the "power" whitening of only the buccal (outer) surfaces of the anterior teeth adversely affects the overall final whitening result, as the natural enamel layers of the teeth (naturally found on both outer and inner surfaces of all the teeth) are naturally somewhat translucent. This allows for the "darker" shade of the inner (lingual) untreated surfaces of the teeth to "show through" to the front surfaces. This naturally occurring optical effect can "bring down" or diminish the overall final whitening effect of these teeth when using the current "power" whitening treatment method.

Advantages of the "in office" or "power" whitening treatment method compared to the "home" treatment include: a. It allows for the more rapid whitening of the teeth compared to the "home" treatment due to the use of more highly concentrated whitening agents. This reduces significantly the over-all treatment time; b. As it is done "in-office", there is less of a non-compliance issue with the patient as is often encountered with the more lengthy "home" treatment; and c. The shorter treatment time tends to minimize the irritation or sensitivity of the teeth, as the teeth are exposed to these agents for a shorter period of time, though some users do experience teeth sensitivity due to the more concentrated strength of the chemical oxidizing agents used in this treatment method and the often encountered unwanted leakage of small amounts of the highly concentrated whitening agents past the protective barriers placed by the dental practitioner onto the oral tissues during the "power" whitening treatment.

Disadvantages of the "in office" treatment method compared to the "home" treatment include: a. As noted above, only the front teeth can be comfortably whitened with the "in office" method, as compared to the "home" treatment which allows for the whitening of both the front and back teeth; b. As mentioned above, the more highly concentrated formulations of the whitening oxidizing agents are more caustic to the hard (tooth) tissue and soft (gums, oral mucosa, tongue) tissue of the mouth and so require the application of special hand-applied gingival and oral mucosal barriers by professional dental staff under the supervision of a dentist or by the dentist him/herself on the gingival and oral mucosal tissues of the areas to be treated in order to protect them from these highly concentrated whitening chemicals. This is a time-consuming procedure that often needs to be reapplied during treatment to properly protect the soft tissues of the mouth form these highly concentrated whitening agents. Even with all this isolation effort, as mentioned above, it is typical to find some leakage and burning of the oral tissues of the patient resulting in temporary pain and discomfort to the patient; c. Due to the inaccessibility of the posterior teeth and difficulty (due to the cheeks and tongue) of the posterior areas of the mouth, these whitening treatments invariably are restricted or limited (due to the extreme difficulty of protecting the oral soft tissues surrounding the posterior teeth) to the anterior segments of the mouth; d. Whitens mainly the front (buccal) surfaces of the anterior teeth and only rarely is used to whiten the inner (lingual) surfaces of the anterior teeth; and e. It is common to observe a more marked "rebound" effect (loss of whitening result) after treatment with this "in office" treatment method as compared to the "home" treatment method. This is due to the short duration of treatment (as compared to the much longer treatment time of the "home" treatment method) and the resultant rehydration of the teeth after treatment (the "power" whitening process tends to temporarily dehydrate the teeth which temporarily potentiates the initial whitening result). This means that the typical final "whitening" result using the "power" whitening technique is significantly poorer then the final "whitening" result that can be obtained when the patient is highly compliant and uses the "home" whitening technique properly.

SUMMARY OF THE INVENTION

There is provided, in accordance with an embodiment of the present invention, a device, method and system for aiding teeth whitening. The device may include a mouthpiece suitable for implementing a dental treatment, wherein the mouthpiece includes one or more stock dental cover layers suitable for forming a treatment cavity having a vacuum, wherein the dental cover layers includes a layer over the upper teeth and/or a layer over the lower teeth; and one or more treatment supply layers wherein the treatment supply layer has one or more flow channel in fluid communication with the treatment cavity so that the treatment supply layer can deliver and/or remove one or more treatment fluids to or from the treatment cavity.

In some embodiments, the dental cover vacuum is formed using a continuous or selectively sustainable sealing mechanism that includes a sealing rim formed of a compressible material in conjunction with one or more sealing plugs attachable to the rear opening(s) of the dental cover layer, wherein the sealing mechanism sufficiently seals the treatment cavity.

In some embodiments, the sealing mechanism is adapted to prevent saliva from entering the treatment cavity and is adapted to prevent treatment material from exiting the treatment cavity.

In some embodiments, the treatment supply layer includes one or more heaters for heating a treatment material, for heating at least a portion of the treatment cavity; or both.

In some embodiments, the device includes a handle integrated into the treatment supply layer suitable for: inserting the one or more dental cover layers over the upper and/or lower teeth, for adjusting the position of the one or more dental cover layers, for removing the dental cover layers after a dental treatment is completed, or any combination thereof.

In some embodiments, the device includes a power line for delivering an electrical current to the treatment supply layer and one or more tubes for delivering and/or extracting one or more treatment materials to the treatment supply layer, the handle includes the power line; or both.

In some embodiments, the dental cover layer covers the gum ridges.

In some embodiments, the device includes two dental cover layers for covering the upper teeth and the lower teeth; at least one treatment supply layer interposed between the two dental cover layers to enable the upper teeth and lower teeth to be treated simultaneously; wherein the device includes one or more breathing vents in the treatment supply layer suitable for providing an air passage into and out of the mouth during a dental treatment.

In some embodiments, the handle includes one or more inflow tubes for flowing one or more treatment materials into the treatment supply layer(s); and one or more outflow tubes for flowing one or more treatment materials out of the treatment supply layer(s).

In some embodiments, the mouthpiece may include: one or more delivery holes for flowing a treatment material from the treatment supply layer to the treatment cavity, and one or more drainage holes for flowing a treatment material from the treatment cavity to the treatment supply layer, and wherein the treatment supply layer includes one or more delivery channels for transporting a treatment material from an inflow tube to the treatment cavity and one or more drainage channels for transporting a treatment material from one or more drainage holes to an outflow tube.

In some embodiments, the dental cover layer includes a compressible cavity plug suitable for sealing the cavity to prevent material flow out of the rear sides of the vacuum forming layer.

In some embodiments, the device includes one or any combinations of the following design features: the dental cover layer incorporates a scrolled cut out apron design to conform to the gum ridges; the treatment supply layer includes one or more individually controllable heating zones; the dental treatment layer is between upper and lower dental cover layers and is shaped to mirror a hinge axis angle to facilitate natural jaw movement.

In some embodiments, the above described vacuum is formed via the treatment supply layer, by reducing the pressure in the dental treatment cavity below ambient pressure.

In some embodiments, the device may include a pumping system, for pumping one or more treatment materials into the mouthpiece; a multi-position flow control module; and a control unit for automating the dental treatment.

In some embodiments, the device includes a dental gum guard component for additional protection against treatment materials.

In some embodiments, the device includes a dental gum guard component which includes a gum treatment layer on its inner surfaces for the delivery of one or more therapeutic material to the gums.

According to some embodiments, a dental gum guard is provided, that may include a flexible surgical arch shaped drape designed to conform substantially to the gum ridge anatomy, and having pre-configured cut-out holes for customized insertion over the teeth which acts to provide a dry field.

In some embodiments, the dental gum guard includes a treatment material layer on one or more surfaces, wherein the treatment material is suitable for neutralizing treatment materials.

In still further embodiments, a method is provided for executing dental treatments, including positioning a mouthpiece including one or more dental cover layers over upper and/or lower teeth; applying a vacuum to the dental cover layer so that a sealed treatment cavity having a pressure below ambient pressure is formed around the teeth; and flowing one or more treatment materials into the sealed treatment cavity.

In some embodiments, the process includes one or any combination of the following steps: setting up a pump module to connect to a mouthpiece designed for a teeth whitening treatment; configuring treatment settings on a control device coupled to the pump module; applying a flow control module to cause a vacuum between the mouthpiece and the patient's gum ridge anatomy; apply flow control module to automatically manage delivery of materials in accordance with said treatment settings, and/or using a flow control module to remove treatment materials from the mouthpiece.

In some embodiments, the method includes a step of applying flow control to change flow patterns during a treatment, in order to optimize conformance to a treatment plan.

In some embodiments, the method includes a step of monitoring the treatment to track conformance to a treatment plan.

In some embodiments, the method includes a step of monitoring the treatment to identify problems during a treatment.

In some embodiments, the treatment supply layer includes a plurality of zones including a first zone and a second zone, wherein the process includes providing different treatment materials to the first zone and the second zone.

In some embodiments, the treatment materials differ with respect to the temperature of the materials, with respect to the concentration of the materials, or both.

The treatment device, according to some embodiments, may be a stock item that may be provided is several stock sizes, and which is either reusable or a one-time throw-away item may include a single dental arch or double dental arch mouthpiece with breathing tubes incorporated into the body of the device that allow the patient to breathe through the mouth when the double dental arch mouthpiece is inserted into the oral cavity. The mouthpiece device has flexible side walls with a circumferential deformable apron of unique design that adapts to the upper and lower alveolar ridges of the mouth. Each arch formed well contains at its distal end (right and left sides) a rear seal plug. The plug is made of a highly deformable material which when bitten into tightly conforms to the anatomy of the crown segment of the tooth that is biting into it. The plugs in conjunction with the uniquely designed deformable circumferential apron of the rim wells allows for the mouthpiece device to closely adapt the upper and lower alveolar gum ridges and the distal most teeth (right and left side) creating an intimate continuous or selectively sustainable seal of the mouthpiece to these structures.

The mouthpiece device also incorporates in its middle layer, multiple flow channels with outlets and inlets and multiple heating elements in various different arrays along its various surfaces whose temperature can be individually controlled by a microprocessor unit contained within a control unit. In some embodiments, these heating elements may be printed circuit resistors. Metal pins may be connected to these pins, and the pin heads may come into contact with the treatment cavity, thus effectively transferring heat generated by the resistors to the treatment cavity and the treatment material contained within it. The microprocessor unit can control electrical power, time duration, alarms, sensors, individual or multiple heat emitting elements, pumps, motors, and other controls. Several different types and sizes of disposable customizable or stock separate gum protector/guard elements can be inserted into the mouth prior to inserting the mouthpiece and used in conjunction with the device.

The mouthpiece may have an arch shape with opposing left and right ends configured to fit over dental arches.

A pump component can be used to create a vacuum within the mouthpiece device. Differing concentrations of chemical whitening agents can be pre-heated to a specific controlled temperature in a disposable heating chamber and then delivered in a controlled manner via said disposable pump and a set of disposable flexible tubing connected to the mouthpiece device. Pressure sensors are integrated into the system to monitor volume and flow rate of the gel and vacuum seal integrity of the mouthpiece in the mouth. The whitening gel agents can similarly be removed from the device in a controlled manner by said system. Similarly, fresh water can be delivered to and removed from the mouthpiece device in order to rinse or flush away any remaining gel residue from the teeth and the inner surfaces of the mouthpiece.

To achieve the above, a motor-driven rotating multi-position flow control valve incorporated into the pump and controlled by the microprocessor of the control unit allows for; 1. the creation of a continuous or selectively sustained vacuum in the mouthpiece 2. the delivery to the mouthpiece, and removal from the mouthpiece of the whitening gel 3. a unique "closed-circuit" steady or pulsatile dynamic flow of the gel within the mouthpiece 4. delivery and removal of water to the mouthpiece to effect a rinsing or flushing of any residual gel from both the teeth surfaces and the inner surfaces of the mouthpiece.

An optional tooth shade matching sensor unit to record pre and post-treatment tooth shade values may be incorporated into the control unit. Additionally, a removable band with a sensor that is connected to the control unit and which measures certain vital signs (such as the pulse rate) of the patient may be connected to the patient to monitor the comfort level of the patient throughout the treatment.

According to various aspects of the invention, the device for providing a dental treatment may include a deformable gum sealing portion for covering a gum; a distal tooth sealing portion, wherein the gum sealing portion and the distal tooth sealing portion define a gap between at least a portion of the device and the tooth over which it lies; and at least one fluid conduit portion for passing a fluid into or out of the treatment cavity; wherein the placement in a patients mouth over a plurality of teeth the gum sealing portion contacts and deforms against a gum of the patient for forming intimate contact with the gum, and the distal tooth sealing portion deforms against distally located for substantially defining a seal at the distal tooth, so that a fluid can be introduced, removed, or both from the treatment cavity while maintaining a seal with the deformable gum sealing and tooth sealing components.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIG. 2a is a front view of an example of a mouthpiece device 1, according to some embodiments;

FIG. 2b is a side view of an example of a mouthpiece 1, according to some embodiments;

FIG. 2c is a top view of an example of a middle layer, according to some embodiments;

FIG. 2d is a bottom view of an example of a middle layer 4, according to some embodiments;

FIG. 3 is a close-up top view of an example of an anterior segment of the middle layer, according to some embodiments;

FIG. 8a is front (labial) view of an example of a mouthpiece, according to some embodiments;

FIG. 8b is a close up inner side (facing the surface of the mouthpiece, according to some embodiments;

FIG. 8c is a close up outer (facing away from the surface of the mouthpiece 1 not depicted) view of the quick attach connector, according to some embodiments;

FIG. 9a is an angled view of one side of an example of a pump mechanism assembly, according to some embodiments;

FIG. 9b is an angled view of the opposite side of FIG. 9a, according to some embodiments;

FIG. 9c is a top view of the pump mechanism assembly, according to some embodiments;

FIG. 9d is a front view of the pump assembly, according to some embodiments;

FIG. 13a is a front vertically stacked view of the upper gum guard 59 and the lower gum guard 60, according to some embodiments;

FIG. 13b is a front view of the upper jaw, according to some embodiments;

FIG. 13c is a front view of an example of a mouthpiece device 1 inserted between the upper 24 and lower 25 jaws respectively, according to some embodiments.

Figure 1A:
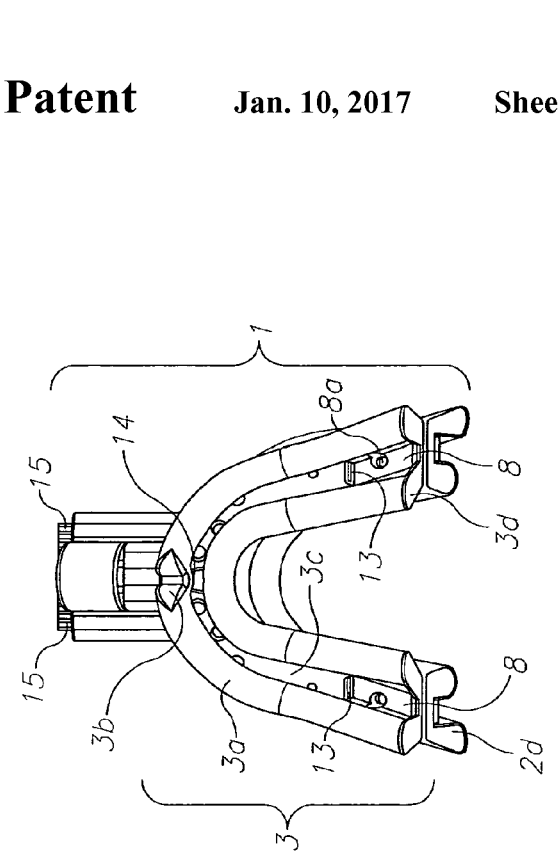
FIG. 1a is a top view of an example of a mouthpiece device 1, according to some embodiments, wherein is depicted a dental arch shaped vacuum forming layer, constructed from flexible material with compressible rims designed to form a treatment cavity over the upper or lower teeth and gum ridges.

It will be appreciated that for simplicity and clarity of illustration, elements shown in the drawings have not necessarily been drawn to scale. For example, the dimensions of some of the elements may be exaggerated relative to other elements for clarity. Furthermore, certain quantities of elements have been depicted, in accordance with specific embodiments, however other embodiments may be provided with fewer or more elements, such as holes, pins, heating elements, tubes etc. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

Preferred dental treatments employ one or more chemicals, such as peroxides that whiten the teeth by one or more chemical reactions. Embodiments of the present invention enable increasing the efficiency and effectiveness of the dental treatments, by using a vacuum to create a sealed treatment cavity or zone where treatment materials may be optimally applied, and me also be prevented from escaping outside of the scaled treatment cavity. Non-limiting embodiments of the invention include a dental treatment device, method and system, such as for teeth whitening.

Embodiments of the present invention incorporates features which take into consideration one or any combination of the advantages and disadvantages listed above for the two described treatment methods (such as power in office and home custom tray whitening) and materials currently in use in the dental field. Embodiments of the present invention include a dental treatment mouthpiece that may include a single or double dental arch. The mouthpiece may be used for providing a whitening treatment. The mouthpiece may include one or more dental cover layers for covering the upper teeth and/or the lower teeth. A dental cover layer preferably is an arch, such as a dental arch, configured for fitting over either the bottom teeth or the upper teeth. For example, the mouthpiece may include an upper dental cover layer and a lower dental cover layer (e.g., the mouthpiece may include a double dental arch). The dental cover layer may have a dental arch well that covers the teeth. A particularly preferred mouthpiece includes two dental cover layers, each having a dental arch wells, where the two dental cover layers are co-joined to create a single device. It will be appreciated, according to the teachings herein, two co-joined dental cover layers may be joined via one or more additional layers, such as one or more treatment supply layers.

The mouthpiece, according to some embodiments of the present invention, allows for the use of generic or stock mouthpieces in patients, such that the variable widths and lengths of the patients' full dental arches can be handled, without the need to fabricate a custom made mouthpiece for each patient. When using such stock mouthpieces, embodiments of the present invention enable the maintenance of a continuous seal of the mouthpiece to the given dental arch onto which it is placed. The distal plugs are highly deformable so that when the patient is instructed to bite down into the mouthpiece, the plugs will readily deform around the coronal segments of the terminal teeth. This intimate fit of the improved mouthpiece of the present invention to any given dental arch is independent of the length and width of the dental arch to which it is to be fitted and independent of the position of the right or left terminal teeth of any given dental arch to their respective retro-molar pads.

The device, the dental treatment mouthpiece (e.g., the whitening mouthpiece), or both may be reusable or disposable after a single use. The mouthpiece may be constructed in various generic or stock sizes (e.g., small, medium, large, extra-large) or may be customized, for both the upper and lower teeth. The mouthpiece may include one or more heating elements for heating a dental treatment fluid (e.g., a dental treatment fluid suitable for chemically whitening teeth), for heating a zone of the dental cover layer, or both. For example, the dental treatment mouthpiece may have a plurality of zones each heated by a different heat element. Each zone may be heated to the same temperature so that teeth receive the same dental treatment. In various aspects of the invention, two or more zones are heated to different predetermined temperatures so that teeth receive different treatments. The use of different predetermined temperatures may beneficially result in teeth having a more uniform color (e.g., between different teeth or between different regions of the same tooth).

The device may be employed in a system including one or more control units, such as a control unit including a microprocessor. The control unit may be an external control unit. The control the control unit may control the temperature of one or more heating elements (e.g., so that multiple zones have a predetermined temperature that may be the same or different). The control unit may control a mouthpiece having a double dental arch each having a dental arch well so that the simultaneous whitening of both the upper and lower teeth are controlled.

An arch of the dental mouthpiece (e.g., each arch of a co-joined double arch mouthpiece) preferably has a dental cover layer with an arch-shaped well or other design suitable for forming a treatment cavity that may contain one or more dental treatment fluids. For example, the arch-shaped well may contain a dental fluid that includes a predetermined concentration of an active ingredient. The active ingredient may be any chemical that is suitable for whitening teeth in situ. A particularly preferred active ingredient includes one or more peroxides. The two dental cover layers of a double arched mouthpiece may have wells that contain the same concentration of active ingredient or different concentration. A single well may have multiple zones or regions with different concentrations of an active ingredient. It will be appreciated that the mouthpiece according to the teachings herein may be employed for providing large differences in concentrations of a whitening agent. The difference in concentration in the active ingredient (e.g., the whitening agent, which may be a peroxide, such as hydrogen peroxide) between two dental cover layers and/or between two zones or regions may be about 0% or more, about 5% or more, about 15% or more, or about 25% or more. It will be appreciated that even larger variations in concentrations may be employed according to the teachings herein. For example, the difference in the concentration of the active ingredient may be about 35% or more. The active ingredient may be activated or have a reactivity that is otherwise accelerated or potentiated (e.g., catalyzed or otherwise) by heat. The treatment fluid (e.g., the treatment fluid including an active ingredient may be delivered via a pumping system (e.g., an automatic pumping system), via a vacuum, or both, into the well sections of the mouthpiece. Preferably, while in the well, the treatment fluid substantially covers the natural crown portions of the teeth (e.g., the teeth subject to a treatment). Alternatively, while in the well, the treatment fluid substantially covers that portion of the gum tissue surrounding the crown portions of the teeth (e.g.; the gums subject to a treatment).

The sealed compartment (i.e. sealed treatment cavity) around the teeth formed by the well of the dental cover layer may be employed for delivering one or more treatment materials to the crown portions of a plurality of teeth. For example, a sequence of two or more different treatment fluids may be passed through the sealed compartment. Without limitation, the treatment fluids may include one or more preparation fluids, one or more active treatment fluids (e.g., one or more whitening treatment fluids), one or more neutralization fluids, one or more rinsing fluids, or any combination thereof. Preferably the treatment fluids include one or more whitening treatment fluids and one or more rinsing fluids. The whitening treatment fluid may include any art known active and/or any non-active ingredients for whitening teeth. Without limitation, the whitening treatment fluid may include one or any combination of the features of the fluid compositions described in U.S. Pat. No. 7,189,385 (see e.g., column 1, line 2 through column 18 line 40); U.S. Pat. No. 6,770,266 (see e.g. column 2, line 9 through column 6, line 35), U.S. Pat. No. 6,746,679 (see e.g., column 1, line 13 through column 11, line 18); U.S. Pat. No. 5,668,934 (see e.g., column 1, line 33 through column 16, line 10); U.S. Pat. No. 7,601,002 (see e.g., column 1, line 11 through column 16, line 8); US Patent Application Publication Nos. 2008/0063612 (see e.g., paragraphs 11 through 165); 2005/0214720 (see e.g. paragraphs 10 through 102); and 2004/0185013 (see e.g., paragraphs 3 through 150); each incorporated herein by reference. Any of the treatment fluids may be a liquid that flows under gravitational forces, or a gel that does not flow under gravitation forces. The treatment fluid preferably can be pumped and/or flows under a vacuum. Preferably any treatment fluid that may be damaging to soft tissue of the oral cavity (e.g., gums or other soft tissues) is in the form of a sufficiently high viscosity fluid or gel so that the fluid does not flow out of the sealed compartment surrounding the teeth being treated. For example, such treatment fluid may have a viscosity of about 0.1 Pa·s or more, about 1.0 Pa·s or more, about 10.0 Pa·s or more, about 100 Pa·s or more, or about 1000 Pa·s or more.

One or more of the treatment fluids may be heated for decreasing the viscosity, for increasing the reactivity or both. For example, increasing the temperature of the treatment fluid, such as a whitening agent (hereinafter referred to as gel, although high viscosity fluids may be employed according to the teachings herein) may increases the rate of peroxide decomposition to create oxygen free radicals from the gel and so may increase the resultant whitening effect in the enamel surfaces of the teeth. Of course, other treatment materials may be used, including water, salt, gasses, chemical and/or biological medicament solutions, or other materials, compounds etc. Each well (e.g., arch-shaped well) of the dental covering layer may contain one or more inlet holes (e.g., one or more inlet holes on each of the right and left sides of the arch) for the delivery of treatment materials into each well, as well as outlet (i.e., drainage) holes (e.g., either anteriorly or posteriorly) for the removal of treatment materials from each dental arch well. The device may include multiple heat emitting elements arranged and controlled in such a way that the control unit (e.g., the microprocessor control unit) independently controls the temperature of each heat emitting element so as to create separately controlled whitening "zones" and/or a predetermined pattern of custom whitening. The temperature control preferably is selected based on one or more characteristics of the patient (e.g., the initial color and/or the initial color variation The components, devices, systems and methods according to the teachings herein may advantageously be employed in accelerated dental treatments, such as an accelerated whitening treatment. By employing a treatment fluids (e.g., a whitening fluid, such as a whitening gel) having a high temperature, having a high concentration of active ingredient (such as a peroxide), or both, the rate of whitening may be increased so that the treatment is accelerated. It will be appreciated that the whitening treatment may be achieved without the need for photodynamic therapy. An accelerated dental treatment may be accomplished by heating the dental treatment fluid. Although room temperature treatment may be employed, some or all of the treatment fluid preferably is heated to a temperature of about 27° C. or more, more preferably about 30° C. or more, even more preferably about 34° C. or more, even more preferably about 38° C. or more, even more preferably about 42° C. or more and most preferably about 46° C. or more. Of course, higher or lower temperatures may be used as may be necessary. The treatment fluid in the treatment zones (i.e., in the sealed cavity formed by the dental cover layer) may have a generally uniform temperature or may have varying temperatures. A temperature differential may advantageously be employed between two zones so that the two zones have different treatment rates. For example, two zones within a sealed cavity may have a sufficiently different temperature so that the ratio of the whitening rate in the first zone to the whitening rate in the second zone is about 1.1 or more, preferably about 1.3 or more, more preferably about 2 or more, and most preferably about 4 or more. Of course, different whitening rates may be used as may be necessary. It will be appreciated that similar increases in treatment rates may be achieved using higher concentration of active ingredient in the treatment fluid in one or more of (e.g., all of) the treatment zones.

The devices and systems according to the teachings herein may be used in a process that includes a step of measuring a natural pre-treatment (i.e. baseline) color characteristics of the different teeth of a patient. A treatment for the patient may be determined based on the color of the teeth, based on the color variation of the teeth, or both. According to the teachings herein, the devices, systems and methods of the present invention may advantageously be employed in patients having variability in natural pre-treatment (baseline) color shade value of the different teeth for reducing this variation. In various aspects of the present invention, the ability to achieve a more uniform final whitening (i.e., resulting color) is achieved by controlling the temperature and hence the oxidative activity of a whitening gel in a plurality of zones areas of the mouthpiece device (such as various zones of the dental cover layer. The control of the various zones may effect a varying change in color (e.g., intensity of whitening) of different teeth, different surfaces of the teeth, or both. The heating elements may be positioned in various locations of the mouthpiece to allow for the separate and differential heating of the different surfaces of the teeth) located in each zone. For example, the positioning of one or more heating elements may be selected based on the measured color and/or color variation. One or more of these features may be employed to achieve a more uniform final esthetic whitening result.

The use of a controller capable of separately controlling multiple treatment zones of the mouthpiece (e.g., whitening "zones") or otherwise effecting patterns of whitening within each of the dental cover layers of the mouthpiece may allow a dentist to customize the whitening process based on the patient's individual needs. The controller may allow a dentist to provide the customized treatment in an automated manner.

The dental cover layer(s) preferably has a circumferential rim formed of a sufficiently soft material and arranged so that the rim will compress and deforms to fit snugly against the sides of the alveolar gum ridges of the upper and lower jaws. The rims may thus create a sealed cavity (e.g., formed from the well of the dental cover layer) with the crown of the teeth contained within the cavity.

The improved mouthpiece of the present invention may incorporate one or more air breathing vents. Preferably, the breathing vents are designed to penetrate through a treatment supply layer of the mouthpiece without compromising the ability of this treatment supply layer to flow one or more treatment materials into the wells (e.g., arch-shaped wells) of the dental cover layers, without compromising the ability of this treatment supply layer to drain one or more treatment fluids from the dental cover layer, or both. For example, the breathing vents may be integrated into a treatment supply layer in a manner that allows for flow of one or more treatment fluids into and out of the mouthpiece.

The sealing rims, preferably made of a soft deformable material, may have a unique structural shape, such as a shape that forms a highly deformable apron or circular hook design that acts to seal the mouthpiece device (e.g., the dental cover layer) of the present invention to the alveolar gum ridges. The sealing preferably may be partially or entirely accomplished by a patient biting down onto the mouthpiece. The sealing rims may effectively seal the well of the dental cover layer so that the treatment materials (i.e., the treatment fluids) delivered to the mouthpiece are prevented from leaking into the oral cavity. The sealing may be partially or entirely accomplished by the application of a vacuum. For example, when a vacuum is applied, the sealing rims may be sucked up against the side walls of the gum ridges. A treatment fluid that is pumped into a sealed well of a dental cover layer preferably contacts the respective teeth on the front surface, the top surface, the back surface, or any combination thereof. More preferably, the treatment fluid contacts the teeth on the front and back surfaces. Even more preferably, the treatment fluid contacts the teeth on all of the exposed surfaces. The sealing effect of the highly deformable apron and/or sealing rim may be accomplished or enhanced by the ability of the treatment system to remove (e.g., suck out) the air within the mouthpiece utilizing an external pump in order to achieve a vacuum seal of the mouthpiece to the upper and/or lower alveolar gum ridges of the upper and/or lower jaws.

Due to the fact that there is great variation in the length of the dental arches between individuals, it may be difficult or even impossible to effectively use a generic stock dental arch to effectively seal the rear-most region of the well of the dental cover layer. For example, it may be difficult or impossible to effectively seal the areas corresponding to the terminal right and/or left tooth in any given dental arch. Without a sufficient seal in these areas, the treatment fluid may undesirably leak out of one or more sides (i.e., the right side, the left side or both) of one or both of the upper or lower arch well through these large unsealed openings. Such an unsealed openings (i.e., unsealed regions) may also prevent the creating and/or maintaining of a vacuum seal of the dental wells without providing for some means to seal off these open areas. Forming a vacuum seal between a dental cover layer and a retro-molar pad may face hurdles such as having to select or prepare a dental cover layer of sufficient length and possible contact of the soft tissue of the retro-molar pad with a treatment fluid. To overcome these obstacles, the vacuum seal in the rear of the dental cover layer preferably is made with a molar on each side of the dental arch. Although, this may limit the ability to provide a dental treatment to one or more molars, the aforementioned benefits generally outweigh this concern. Nevertheless, the need to form a sufficient seal (e.g. for maintaining a vacuum) may present particular challenges when sealing over a molar. Surprisingly a sufficient seal has been achieved using a unique distal plug insert. To prevent such leakage of the treatment material and to allow for the ability to create and maintain a continuous or selectively sustained vacuum in the mouthpiece, various teachings of the present invention may incorporate one or more distal plug inserts (i.e., distal sealing plugs). The term "selectively sustained vacuum" may refer to the ability of a user or practitioner to determine how long to maintain the vacuum, initiate and release vacuums multiple times in a treatment etc. Preferably distal plug inserts are employed with both ends of each dental cover layer. The distal plug inserts may be designed and or positioned to uniquely attach into the rear left and right ends of the well of the dental cover layer. Preferably, the distal plug inserts effectively seal these openings. For example, the distal plug inserts may seal the openings when the patient bites down onto the mouthpiece.

The distal plug inserts are preferably made of a material that is sufficiently deformable so that an insert intimately contours the variable tooth anatomy of one or more of the rear teeth, such as the right and left terminal teeth (e.g., despite the variability between different individuals with respect to the length of their dental arch). The distal plug insert may be made of a polymeric material. Preferred polymeric materials for the distal plug insert are elastomeric so that after being deformed the distal plug insert will generally return to its original shape. The distal plug insert may be made of an elastomeric material. The elastomeric material have a crystallinity of about 0%, however elastomeric materials having a higher crystallinity may be employed (e.g., about 0.5% or more). Preferred elastomeric materials have a crystallinity of about 15% or less, about 10% or less, or about 5% or less. The distal plug insert may be made of a foamed material. Preferred foamed materials have a close cell foam structure. Typically, elastomeric materials have a glass transition temperature of about 10° C. or less, about −10° C. or less, or about −40° C. or less. The elastomeric material preferably has a sufficiently low durometer so that the distal plug insert can be deformed to conform to a surface of a molar. The elastomeric material preferably has a Shore A durometer of about 60 or less, more preferably about 50 or less, even more preferably about 40 or less, and most preferably about 30 or less. The elastomeric material of the distal plug insert may have a sufficiently high durometer so that the insert does not tear during storage and use. For example, the Shore A hardness may be about 2 or more, about 5 or more, or about 8 or more. The elastomeric material preferably is sufficiently cured so that material does not flow. The elastomeric material may be formed of any polymer, such as a polymer including carbon backbone or a polymer including a silicon backbone. By way of example, the elastomeric material of the distal plug insert may include a silicone rubber, such as an RTV silicone rubber capable of vulcanizing at room temperature, or an HTV silicone rubber capable of vulcanizing at one or more elevated temperatures. The elastomeric material may prevent the need to remove residual material after providing a dental treatment, such as required when using wax or other moldable materials. As such, the distal plug insert may function without the need for a moldable material. The elastomeric material may be a generally solid material (i.e., having a void content of about 10 volume % or less, about 5 volume % or less, or about 1 volume % or less). Such material may be essentially free of, or entirely free of voids. Suitable elastomeric materials may be a cellular material, such as a material having an open cell foam structure, a closed cell foam structure, or both.

The distal plug insert preferably has a sufficient width so that it capable of forming a seal along the top surface of a molar going from the back of the tooth to the front of the tooth. The distal plug insert preferably has a sufficient length so that it will generally seal at least one molar in an individual, regardless of the length of the individuals dental arch length. A long distal plug insert may also enable forming a seal in individuals who have undergone a molar extraction. The length of the distal plug insert preferably is about 2 mm or more, more preferably about 4 mm or more, even more preferably about 6 mm or more, even more preferably about 8 mm or more, and most preferably about 10 mm or more. It will be appreciated that the distal plug insert may be interchangeable so that a distal plug insert of sufficient length and/or width may be selected for providing optimal sealing based on one or more features of the patients' dental arch (such as its length).

Each dental arch mouthpiece device includes one or more treatment supply layers. The treatment supply layer may provide one or more treatment fluids to a dental cover layer, may provide heat to a dental cover layer, or both. If the mouthpiece includes two dental cover layers, each dental cover layer may be have a separate treatment supply layer, or a single treatment supply layer may be employed for both dental cover layers. For example, a single treatment supply layer may be positioned between two dental cover layers. The treatment supply layer may contain built-in flow channels or tubes capable of flowing one or more treatment fluids. The flow channel or tubes of treatment supply layer preferably course throughout this layer of the mouthpiece. The treatment supply layer preferably has one or more (e.g. two or more) inlet holes for delivering a fluid to a well (e.g., sealed cavity) of a dental cover layer. The treatment supply layer preferably has one or more (e.g., two or more) outlet holes for removing a fluid from a well (e.g., sealed cavity) of a dental cover layer. It will be appreciated that flow directions may be changed so that an outlet hole can function as an inlet hole, so that an inlet hole can function as an outlet hole or both. A treatment supply layer that services upper and lower dental cover layers may have (1) one or more holes (e.g., inlet and outlet holes) in the floor of the treatment supply layer for providing a fluid communication with the cavity or well of the dental cover layer of the lower teeth; and (2) one or more holes (e.g., inlet and outlet holes) in the ceiling of the treatment supply layer for providing a fluid communication with the dental cover layer over the upper teeth. The flow channels or tubes preferably transport and substantially evenly distributes one or more treatment fluids to the dental cover layer. The treatment fluid may be any art known treatment fluids, such as described herein. For example, the treatment fluid may include a whitening material (such as a gel material), water, air, medicinal materials, therapeutic materials, cleansing materials, rinsing materials, or any combination thereof. The treatment supply layer may deliver one or any combination of the treatment fluids into the wells (e.g., the dental arch wells) of the dental cover layer. As such, the treatment supply layer may effectively bathe one or more (e.g., all of the surfaces of the teeth in the well and covered by dental cover layer(s) with the whitening gel or other treatment materials. Preferably the channels or tubes are capable of delivering and/or removing a plurality of treatment fluids, such as water or air.

The components, devices, systems, and process according to the teachings herein may be employed in a dental treatment for providing a treatment to one or more teeth, for providing a treatment to the gums, or both. These components, devices, systems, and processes may find application in teeth whitening; antibiotic treatment, antimicrobial treatment, fluoride treatment, or any combination thereof. It will be appreciated that other applications in the field of dentistry may find use of the features according to the teachings herein. The dental treatment may be a generally short treatment, such as for about 10 minutes or less, or may be a generally long treatment, such as for greater than 10 minutes, preferably about 20 minutes or more, more preferably about 30 minutes or more. It will be appreciated that the duration of the dental treatment will typically be about 3 hours or less, more preferably about 2 hours or less, and most preferably about 1 hours or less. Dental treatments of duration greater than 3 hours are also anticipated (e.g., from about 3 hours to about 8 hours, such as during the night sleep hours). A vacuum may be applied to the dental cover layer for a substantial portion (e.g., at least 50% of the duration, at least 70% of the duration, at least 80% of the duration, or at least 90% of the duration) of the treatment time. The dental cover component surprisingly is capable of maintaining a vacuum for such long durations even when the dental cover component is a stock generic cover (i.e., not a custom made cover).

As mentioned above, according to some embodiments, a dental treatment system may include a pumping component for pumping one or more treatment fluids. For example, the pumping component may be in fluid communication with a mouthpiece according to the teachings herein. Preferably the pumping component is in fluid communication with the treatment supply layer of the mouthpiece. The system may include a control unit for controlling the pumping component. A pumping component may be incorporating into the housing of an external control unit or may be a separate element. The pumping component may incorporate a heating chamber for pre-heating the treatment fluid to one or more predetermined temperatures. For example a control unit including a microprocessor may monitor and/or control the temperature of a treatment fluid. The control of the temperature preferably employs a feedback loop. Using the temperature control, the temperature of a treatment fluid being delivered to the mouthpiece may be controlled. A heating chamber may advantageously enables a practitioner to utilize a whitening fluid (e.g., a whitening gel) immediately from storage, and thus eliminate the need for a step of defrosting the whitening fluid, a step of warming the whitening fluid, a step of preparing the whitening fluid for usage in a dental treatment, or any combination thereof. As such, the dental treatment processes according to the teachings herein may be free of combination or all of the aforementioned step.

The treatment delivery system may include one or more control valves, and preferably one or more multi-position flow control valves. The multi-position flow control valve preferably is in fluid communication with the pumping component. For example, the control valve may be incorporated into the pumping unit. However, a control valve may be positioned outside of the pumping unit. The control valve may be manually operated or may be operated automatically. For example the control valve may be motor-driven, may be controlled by a controller, or both. The multi-position valve may rotate to different positions, wherein each position of the valve allows for different flow routes of treatment materials through the flexible tubing of the system. The valve may be rotated by being engaged by a drive shaft of a motor that is controlled by the microprocessor unit, or by other means. For example, the microprocessor may controls the rotational position of the valve and thus allow, depending on the valve's position, different flow patterns. Examples of flow patterns that may be achieved using a control valve include: 1. providing a fluid connection between a vacuum line and a the mouthpiece for the removal of the air from the mouthpiece, for creating a vacuum seal of the mouthpiece to the gum ridges, or both; 2. providing a fluid connection between a treatment fluid and the mouthpiece for delivering the treatment fluid to a sealed cavity (e.g., a sealed cavity formed by a dental cover layer); 3 removing a treatment fluid from the mouthpiece; 4. Creating a "closed circuit" flow of a treatment fluid within the mouthpiece (e.g., where the flow is a dynamic turbulent or a convection type flow); 5. providing a fluid connection between a rinsing fluid (such as water, or a water solution) and the mouthpiece for the delivery of the rinsing fluid and removal of the rinsing fluid from the mouthpiece (e.g., in order to rinse or flush a treatment fluid from the teeth surfaces and the inside surfaces of the mouthpiece); and providing a fluid connection between a neutralizing fluid and the mouthpiece for the delivery of a neutralizing fluid to the mouthpiece for neutralizing a treatment fluid. One or any combination of the aforementioned steps may be controlled by a single control valve, or by a plurality of control valves.

The closed circuit flow mode may allow for the treatment fluid to circulate in the mouthpiece device of the present invention. This flow can be continuous or sporadic (e.g., pulsed or intermittent). For example, when whitening fluid is flowing in a turbulent manner within the sealed cavity formed by the dental cover layer, so that the amount of chemically active treatment fluid that contacts the enamel surfaces of the teeth is greatly increased compared with the case where the treatment fluid is delivered into the mouthpiece and remained statically in place during the whitening treatment. This convection type flow of the treatment fluid around all the enamel surfaces of the teeth increases the whitening potential of a fixed volume of treatment fluid that is delivered to the mouthpiece. This is exactly analogous to the higher heat flux when heating foods in a convection oven. For example, by flowing treatment fluid contained in the mouthpiece device around the teeth in a turbulent manner (just as hot air flows in a convection oven), the system increases significantly the volume of chemically active whitening fluid, delivered to the mouthpiece, that can come in contact with all the enamel surfaces of the teeth. Increased volume of chemically active whitening fluid in contact with all enamel surfaces of the teeth results in significantly increased whitening effect of the fluid into all these enamel surfaces of the teeth.

In another embodiment, sporadically flowing a treatment fluid, such as whitening fluid (e.g., gel), in the mouthpiece device allows for the fluid to remain stationary in one particular area or zone of the tray for a set period of time during the treatment between active fluid flow time periods. It will be appreciated according to the teachings herein that all or selected portions of the treatment fluid, such as the static whitening fluid in an area or zone, may then be heated by the individual heating element(s) to a specific temperature in that zone or area of the tray during this static fluid time period. This may advantageously allow for differential whitening activity in each zone or area for each of these static time periods and so allows for differential or "custom" whitening of the teeth located in each zone or area of the mouthpiece device.

As mentioned above, the flow of the treatment fluid may employ a pump component, such as pump component controlled by a microprocessor, in a sporadic or pulsing manner for a given interval of time. This may allow for alternate static or convection flow of the treatment materials (around the teeth) for set periods of time in the mouthpiece device.

The systems and methods may employ one or more pressure sensors for measuring a pressure in a tube, for measuring a pressure in a sealed cavity, for measuring a pressure in a layer of the mouthpiece (e.g., the treatment supply layer, and/or the dental cover layer), or any combination thereof. The pressure sensor(s) may be incorporated into the control unit. Pressure sensor(s) may monitor, for example, the degree of vacuum in the mouthpiece, one or more flow rates, the total amount of treatment materials delivered into, or alternately, removed from the mouthpiece device by the pump, or any combination thereof. A sensor may also monitor the flow rate of a treatment fluid during a "closed-circuit" treatment cycle.

By maintaining a vacuum seal of the dental cover layer of the dental mouthpiece to the alveolar ridges, the peroxidase enzyme naturally found in saliva are substantially or even entirely prevented from seeping into or otherwise penetrating the sealed cavity. This novel vacuum sealing feature of the present invention may effectively protect the chemically active treatment fluids, such as whitening gel, from being chemically deactivated by the salivary enzyme peroxidase. As the treatment fluid's chemical oxidative potential is never substantially compromised by the saliva, the whitening result of the present invention is enhanced.

It will further be appreciated that a pumping component may allow for continuous flow of a treatment fluid into and out of the mouthpiece throughout the treatment. As such, fresh fluid having full chemically activity may be delivered and applied to some or all of the enamel surfaces of the teeth contained within the dental cover layer throughout the treatment. When employed in a whitening treatment, this may significantly increases the whitening result that can be obtained in a set period of time of the present invention compared to a static one-time delivery of treatment materials as is the case in known tooth whitening procedures.

According to some embodiments, flexible tubes may be connected to the pumping component from the fresh and spent treatment fluid containers and a separate set of flexible tubes connected to the pumping component which in turn also connect to separate inflow and outflow tubes integrated into the front of the mouthpiece. These inflow and outflow tubes may be further integrated into an integral handle design of the mouthpiece device. Such a pump that may contact fluid having been in the sealed cavity may be a disposable pump so that aseptic conditions are maintained. The pump may incorporate a locking and unlocking attachment feature to allow for the quick attaching and detaching of the optionally disposable pump to engage a motor or motors incorporated within the control unit. Alternatively, a pump that pushes the treatment fluid, such as a peristaltic type pump component may be used. Since this pushes treatment fluids that are contained within the tubing, it can be reusable as it does not come in contact with the active treatment materials.

The set of tubes from the pump assembly to the mouthpiece device may be clipped via a clasping device or small harness to the patient's clothing, patient dental apron, or some element of a dental chair or other fixing point so that they any drag they create on the mouthpiece is reduced or eliminated, so that the tubes are neatly organized, or both. The tubes and a power cable may be further attached to a quick-attach connector which snaps into the integrated handle of the mouthpiece device of the present invention.

Another aspect of the invention is directed at a separate disposable gum protector component. The gum protector component may be used with a dental treatment fluid. The gum protector component may be employed in a process of treating teeth with one or more fluids for whitening teeth. The gum protector component may provide a sufficient barrier for the gums so that highly active treatment fluids may be employed. The gum protector component may be designed for insertion onto the alveolar gum ridge(s) of the upper jaw, the lower jaw, or both. The gum protector component preferably is inserted into the oral cavity prior to the insertion of the mouthpiece into the oral cavity. For example, the gum protectors/guards may act to isolate both the maxillary and mandibular gum tissues from even highly concentrated hydrogen peroxide whitening gels that will be delivered into the well(s) of the mouthpiece device, or other potentially harmful treatment materials. The gum protector component may sufficiently the gums so peroxide having a concentration of about 15% or more, about 25% or more, about 35% or more, or about 45% or more.

The gum protector component may be provided as a kit including a plurality of different size gum protector components. The gum protector component may be sufficiently pliable so that only a few different sized stock generic gum protector components are required to treat the majority of patients. For example, the kit may include gum protector components having about 2 or more different stock generic sizes, preferably about 3 or more different sizes, and more preferably about 4 or more different sizes. The number of different stock generic sizes preferably is about 10 or less.

The separate and disposable gum protector (i.e., gum protector component, or gum guard component) in one of its embodiments may be comprised of two distinct layers which can be securely adhered to each other. As an example, the gum protector's main body may be made of a stretchable polymeric material. Preferred polymeric materials have an elongation at break of about 100% or more, more preferably about 200% or more, and most preferably about 300% or more. Preferred polymeric materials have a sufficiently low tension set so that the material recovers its initial shape after being stretched. For example, the tension set (measured at room temperature, 10 minutes after stretching the material by 200%) may be about 10% or less, preferably about 7% or less, more preferably about 5% or less, and most preferably about 3% or less. The polymeric material may have a carbon containing backbone or a silicon containing backbone. The polymeric material may be an elastomer. Examples of elastomers that may be employed include silicone elastomers, natural rubber/latex materials, poly-isoprene, styrene butadiene rubber; SEBS rubbers, or any combination thereof. The gum protector component may have a chemical coating or layer that has been applied and fixed to one or more of its surfaces. For example, a layer may be applied to the inner (proximal) surfaces of the gum protector component, so that the layer is in contact with the gum tissues.

The silicone and or rubber body of the gum protector/guard may be shaped to mirror the horse-shoe shape and ridge form of the alveolar gum ridges of the upper and lower jaws so as to adapt quite closely to these oral structures.

The body of the gum protector/guard component may be further modified to allow for multiple cut-outs of varying diameters and varying spacing between them (fully cut out or perforated for selective removal) along the section of said guard which mirrors the location of the center ridge lines of the alveolar ridges and the teeth of the upper and lower jaws. These cut-outs may mirror or conform in their shape to the scalloped form/shape of the gum-line (inter-dental papilla) of the teeth to be treated.

The inner coating of the gum protector/guard component, as noted above may contain various chemical compounds such as a sugar-based gel or spray-on self-adhering coating whose purpose is to provide a chemical neutralization of the active treatment materials, for example peroxide based whitening gel, and so act as a chemical barrier to further protect the gum tissues from the treatment materials. As mentioned above, the gum protector/guard may provide an effective barrier to protect the gums tissues from even very high concentrations of treatment materials, such as, for example, hydrogen peroxide whitening gels of 35% or even higher.

The optionally disposable gum protector/guard component described above may provide a flexible yet snugly fitting barrier to the gums and alveolar gum ridges that can be placed over the teeth and gums to be treated. When positioned in a dental arch in the mouth, the crowns of the teeth may protrude out of the gum protector component while covering the gums. This fitted barrier (the disposable gum protector/guard component) is further shaped so as to also allow for a good fit and seal of the single or double dental arch mouthpiece device's deformable well rims to the both the upper and lower gum protector/guards. This allows for a good seal of the treatment fluid that is delivered into the mouthpiece device and prevents leakage of the treatment materials from the mouthpiece device into the oral cavity (while the gum guard protects the gums).

When the gum protector component is used with a dental treatment layer, the seal of the space around a row of teeth may be further enhanced by the unique deformable flap apron design and rim of the dental cover layer of the mouthpiece. This seal in conjunction with the unique distal sealing plugs, may enhance the ability of the pump to suck out the air from the mouthpiece and create an effective vacuum seal of the dental cover layer to the outer side wall surfaces of the previously placed gum protector components. It will be appreciated that an upper and a lower gum protector component may be employed for protecting each of the upper and lower jaw's gums.

This configuration and relation of these components to each other in the oral cavity effectively and safely isolates the various concentrations of whitening agents applied to the teeth from the soft tissues (gums, tongue, cheeks, palate, oral mucosa) and so may protect these soft tissues from the caustic effects of even highly concentrated formulations of these chemical agents during the improved whitening treatment of the present invention.

Embodiments of the disposable gum protector/guard component allow for adaptation by the dental practitioner of its shape to further adapt the inner edges of the multiple cut-outs to the scalloped gum-line. Varying the cross-sectional thickness of the gum protector/guard allows for it to maintain its shape (thicker areas) as well as allowing for thinner (tapered) edges to the cut-outs and flossing area strips of the gum protector/guard.

This varying thickness design of the gum protector/guard allows the operator to fold in (using a dental hand tool) the thinner edges of the cut-outs into the natural gingival sulcus space (usually three millimeters deep in healthy gum tissue) that exists between the gums and the teeth as well as floss into the proximal spaces of the teeth the flossing area strips of the gum protector/guard and so may provide an even more effective adaptation of the gum protector/guard component to the gum tissues and a better seal between them.

As mentioned above, other embodiments of the disposable gum protector may also include an inner coating which is self-adhering coating when placed in contact the gum tissues. These coatings may include various medicaments or chemical compounds for therapeutic delivery of these various medicaments or compounds to the gum tissues. Further embodiments of the disposable gum protector/guard have wider dental and medical applications wherever what is known in the dental field as a "dry field" is required or advantageous for a given medical/dental procedure. Said gum protector/guard can be utilized in many dental procedures as a replacement for what is commonly known in the dental field as rubber dam.

Additionally, as the disposable gum protector/guard component is not integral to the appliance, it may be provided in several stock sizes to match a given stock sized mouthpiece device and so provide, without the need to customize the mouthpiece or gum protector guard for each patient, an effective isolation of the gums and other soft tissues of the mouth from even highly concentrated formulations of treatment materials without the need to manually apply a hardening foam material as is in common use in the current professionally administered power whitening procedures.

As mentioned above, the disposable gum protector/guard may be a component which is itself a stock item fabricated in various stock sizes, or alternatively, it may be fabricated as a custom made device for each patient using molding and die techniques known in the field.

The single or double dental arch mouthpiece device may also incorporate an outer thermal barrier layer. This layer may act to protect the patient against the heat generated by the activated multiple heating elements during the whitening treatment method of the present invention.

In accordance with some embodiments, an optional tooth shade matching sensor unit may be incorporated into the control unit, which may be used to record pre and/or post-treatment tooth shade values.

It is well known in the medical field that pulse rates can be used to monitor pain/discomfort levels of a subject. An optional adjustable band may be placed on the patient such as a wrist band which is attached to the control unit and which incorporates a sensor for monitoring certain vital signs of the user, such as the patient's pulse rate, throughout the whitening treatment and thereby monitor the patient's comfort levels throughout the treatment.

Another aspect of the invention is directed at a kit including a plurality of mouthpieces, such as a plurality of mouthpieces according to the teachings herein. The kit preferably includes stock generic (i.e., not custom made) mouthpieces and includes mouthpieces having different sizes. The kit may include mouthpieces having different widths for matching with mouths having different widths of the dental arch (e.g., as measured between corresponding left and right molars). The kit may include mouthpieces having different length of arches. It will be appreciated according to the teachings herein that the use of distal sealing plugs may reduce or eliminate the need for mouthpieces having different lengths. By employing a kit of stock generic mouthpieces, the need for custom production of a mouthpiece (e.g., using a dental mold impression) may be eliminated. The kit may include pre-assembled mouthpieces or may include stock generic dental cover layers, such as the dental cover layers according to the teachings herein. The kit may include dental cover layers suitable for lower dental arches, suitable for upper dental arches, or both. The kit preferably includes dental cover layers having different widths use in individuals having dental arches with different widths. The kit may include one or more treatment supply layers, such as a treatment supply layer according to the teachings herein. The treatment supply layer may be suitable for connecting with one or two dental cover layers. The need for dental cover layers having different lengths may be reduced or eliminated by employing distal sealing plugs in the dental cover layer suitable for sealing the rear ends of the dental arch. Preferred kits include mouthpieces and/or dental cover layers having two or more different stock generic sizes, more preferably three or more different stock generic sizes, and most preferably four or more different stock generic sizes. The number of different sizes may be generally large, but preferably is about 20 or more, more preferably about 10 or less, and most preferably about 6 or less.

Treatment Method

A method for executing a dental treatment is provided herein, according to some embodiments, which may include one or more of the following steps: positioning a mouthpiece including one or more dental cover layers over upper and/or lower teeth; and applying a vacuum to the dental cover layer so that a sealed treatment cavity having a pressure below ambient pressure is formed around the teeth; and flowing one or more treatment materials into the sealed treatment cavity.

In a further embodiment, a method for executing a tooth whitening treatment is provided, wherein one or more of the following steps may be executed: configuring a procedure for simultaneous customized tooth whitening; setting up a pump module to connect to a mouthpiece designed for a teeth whitening treatment; configuring treatment settings on a control device coupled to the pump module; positioning the mouthpiece in a patient's mouth; applying a flow control to cause a vacuum between the mouthpiece and the patient's gum ridge anatomy; applying flow control to automatically manage delivery of materials in accordance with the treatment settings; and using flow control to remove treatment materials from the mouthpiece. Of course, other steps or combinations of steps may be used. For example, prior to a treatment, the baseline shades of the respective teeth may be measured, to enable customized treatment of the respective teeth. In addition, dental impressions may be taken to enable construction of a patient specific mouthpiece. In some cases, a gum guard may be used in addition to the mouthpiece, which may be a customized or stock type of guard. In additional cases, treatment materials may be pre-heated prior to treatment and/or may be heated as may be necessary during treatments.

Reference is now made to the respective figures, which describe elements or aspects of multiple embodiments of the present invention. The drawings are provided for illustrative purposes only and are not meant to be limiting.

FIG. 1a is a top view of an example of a mouthpiece device 1, wherein is depicted a dental arch shaped cover layer, sometimes referred to herein as a vacuum forming layer, constructed from flexible material with compressible rims designed to form a treatment cavity over the upper or lower teeth and gum ridges, hereinafter referred to as the upper or lower dental arch well 2. In other words, the negative space contained between the arched walls of the well form what is referred to herein as the treatment cavity. Dental arch well 2 may include, for example, deformable rims 2a, the upper well floor 2c, the upper labial frenulum cut out 2b of the outer wall of the rim 2, and the upper distal deformable plug sealers 7 with their peg holes 7a. Also depicted is a portion of a middle arch shaped layer designed to deliver and remove customized treatment materials to and from the vacuum forming layer, referred to herein as the middle layer or the treatment supply layer. The middle layer may support, for example, an integrated handle 9, heat transfer pin heads 17, 17a, the arch well material delivery holes 13, the material drainage depression hole 14a, one or more electrical connectors, or any combination thereof. The electrical connector may be a printed circuit board(s) 15. The handle 9 may be designed to facilitate positioning of the mouthpiece into the patients mouth, delivery of materials to the mouthpiece, extraction of treatment materials from the mouthpiece, and delivery of power to the mouthpiece etc. By way of example, the handle may have one or more features that facilitate its manipulation, such as a thumb depression 9a.

Figure 1C:
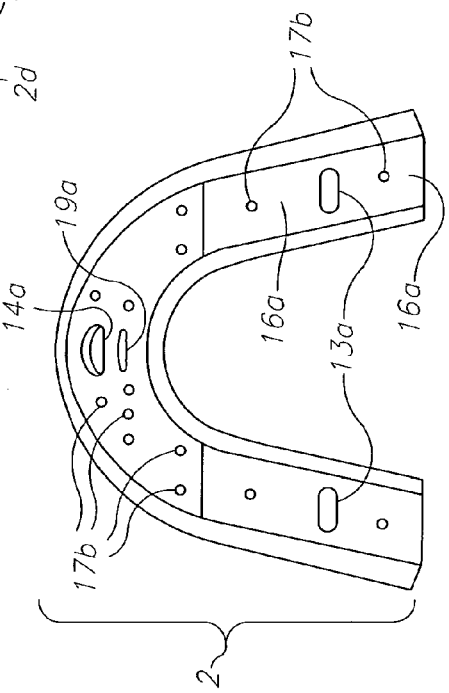
FIG. 1c is an additional view of an example of a mouthpiece device 1, according to some embodiments.
Figure 1B:
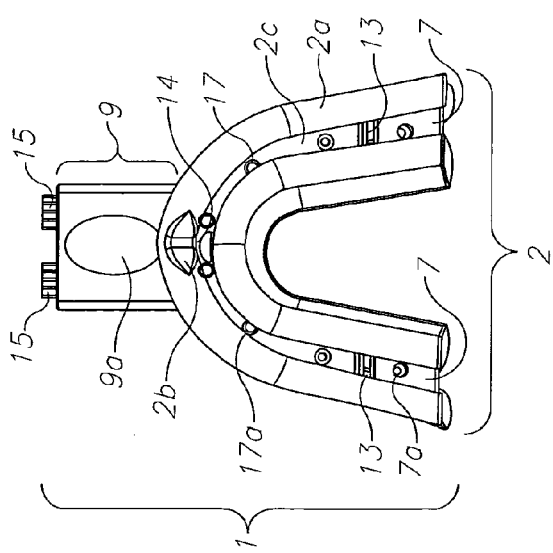
FIG. 1b is a bottom view of an example of a mouthpiece device 1, according to some embodiments.

FIG. 1b is a bottom view of an example of a mouthpiece device 1 wherein are depicted the distal plug sealers 8 and their peg holes 8a, the arch well treatment material delivery holes 13a, the drainage depression hole 14a, a lower dental arch shaped vacuum forming layer, hereinafter referred to as the lower dental arch well 3 with its deformable rims 3a, the lower floor well 3c, the lower labial frenulum cut out 3b, the distal sealing wall 3d of the lower arch well 3, the distal sealing wall 2d of the upper arch well 2, and the printed circuit board(s) 15.

FIG. 1c is a view of an example of a mouthpiece device 1 wherein is depicted the upper dental arch shaped vacuum forming layer, or dental arch well 2, with material delivery holes 13, drainage depression hole 14a, drainage channel hole 19a, arch well peg holes 16a, and arch well heating transfer pin holes 17b.

FIG. 2a is a front view of an example of a mouthpiece device 1 wherein are depicted the upper dental arch well 2, the lower dental arch well 3, the middle layer 4, the in-flow tube 10, the out-flow tube 11, and the air breathing vents 12.

FIG. 2b is a side view of an example of a mouthpiece 1 wherein are depicted the integrated handle 9, the upper dental arch well 2, the lower dental arch well 3, and the middle layer 4. In some embodiments, the middle arch layer is shaped to mirror a hinge axis angle to facilitate natural jaw movement when upper and lower vacuum forming layers are being used. Such an angled hinge axis design of the mouthpiece 1 is adapted to relate directly to the hinge axis relationship of the lower jaw to the upper jaw. The angle of the angled hinge axis design of the mouthpiece (for example the angle between the two vacuum forming layers) preferably is an that is comfortable for a patient to maintain during a dental treatment. Preferably the angle is about 0.5° or more, more preferably about 1° or more, and most preferably about 2° or more. Preferably the angle is about 20° or less, more preferably about 15° or less, even more preferably about 10° or less, and most preferably about 7° or less. It will be appreciated that a higher angle may advantageously be employed to allow for larger breathing vents, to provide more flexibility in the design of the middle layer, or both.

FIG. 2c is a top view of an example of a middle layer 4 wherein are depicted the middle layer top treatment material channel floor 4a with its flow channel side walls 4b, the treatment material inlet holes 13, the heating elements 18, the heat transfer pins 17, the connector pegs 16, the printed circuit board(s) 15, and the in-flow tube 10, and the out-flow tube 11 integrated into the handle 9.

FIG. 2d is a bottom view of an example of a middle layer 4, its flow channel side walls 4b and bottom treatment material channel floor 4c. Also depicted is the drainage channel 19 and its drainage or outflow opening 20 which connects to the out-flow tube 11, the treatment material inlet holes 13, the connector pegs 16, and the air breathing vents 12.

FIG. 3 is a close-up top view of an example of an anterior segment of the middle layer 4 wherein are depicted the drain hole 19 and the drain tube 20 which connects to the out-flow tube 11, the heads 17a and pin ends 17b of the heat transfer pins and the heating elements 18. The heating elements preferably are inserted into or otherwise connected with the printed circuit board 15. The connection between the heating element 18 and the printed circuit board may be Also depicted are the air breathing vents 12. The connection between the heating elements 18 and the printed circuit board 15 may below the channel floor so that the connection is isolated from any fluid that flows through the channel.

Figure 4A:
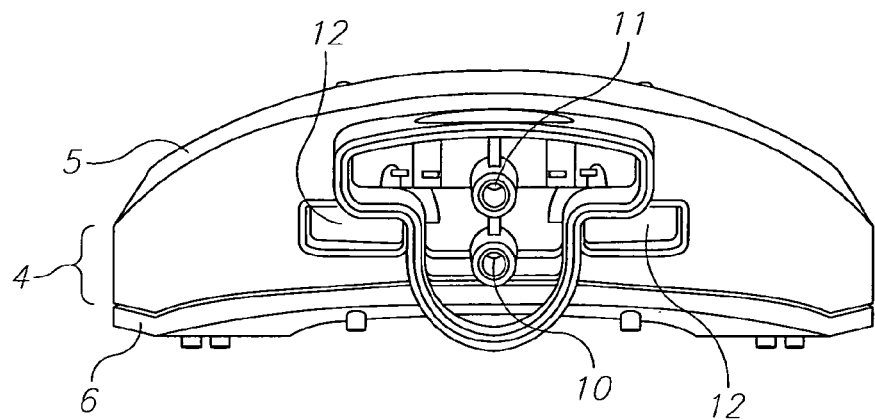
FIG. 4a is a front (labial) view of an example of a middle layer, according to some embodiments.

FIG. 4a is a front (labial) view of an example of a middle layer 4, the middle layer upper cover plate 5, the middle layer lower cover plate 6, the air breathing vents 12 and the in-flow tube 10 and out-flow tube 11.

Figure 4B:
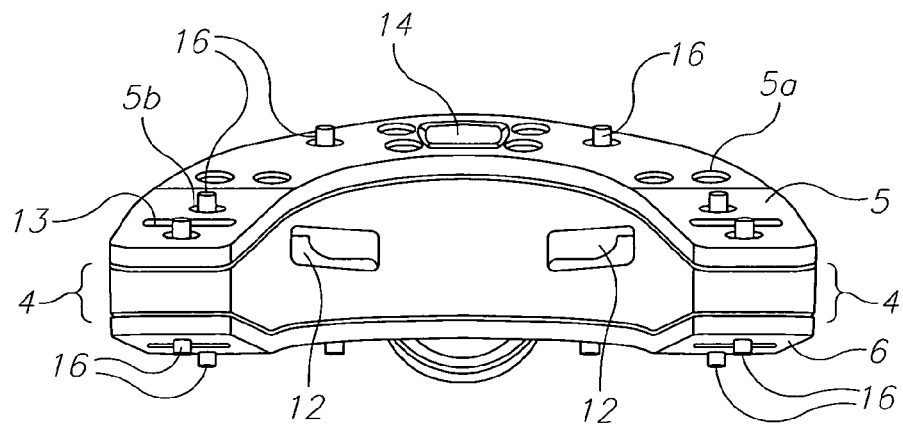
FIG. 4b is an inner (lingual) view of FIG. 4a, according to some embodiments.

FIG. 4b is an inner (lingual) view of FIG. 4a wherein are depicted an example of the inner aspects of the air breathing vents 12, the middle layer upper cover plate 5 with its connector peg holes 5b and its heat transfer pin holes 5a as well as the drain hole depression well 14. Also depicted are the connector pegs 16 which secure the upper cover plate 5 and lower cover plate 6 to the middle layer 4, the treatment material inlet holes 13 which allow for the flow of treatment materials from the treatment material flow channels 4a and 4c inside the middle layer 4 to the upper 2 and lower 3 dental arch wells (not depicted). Also depicted are the air breathing vents 12 which go through the body of the middle layer 4.

Figure 4C:
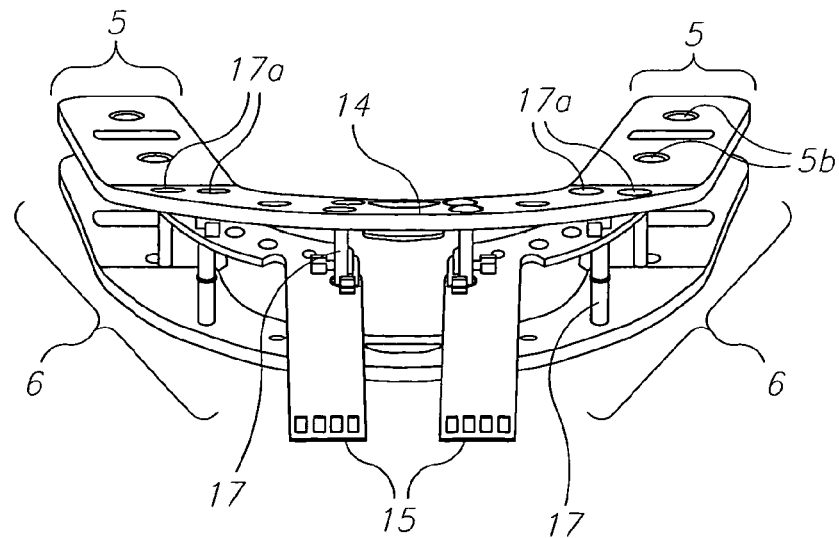
FIG. 4c is a front (labial) view of an example of the device plates and layers, according to some embodiments.

FIG. 4c is a front (labial) view of an example of an upper cover plate 5 and the lower cover plate 6 with the middle layer missing and the structural connections of the heat transfer pins 17 between the upper cover plate 5, the lower cover plate 6 and the printed circuit board 15. Also depicted are the connector peg holes 5b of the upper cover plate 5 and the drain hole depression well 14 of the upper cover plate 5.

Figure 5B:
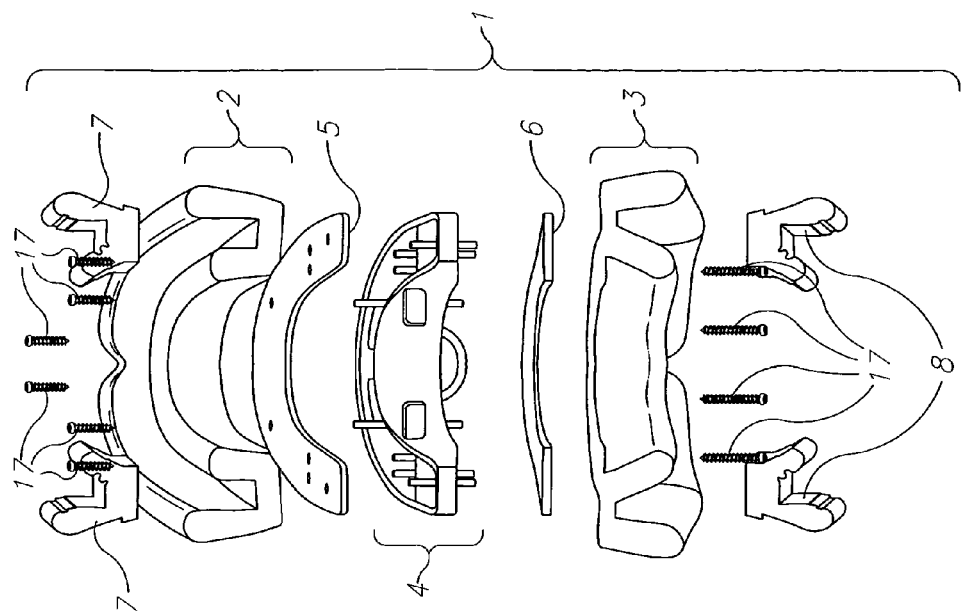
FIG. 5b is a vertical stack blow up back (lingual) view of FIG. 5a wherein are depicted the components which comprise the double dental arch mouthpiece, according to some embodiments.
Figure 5A:
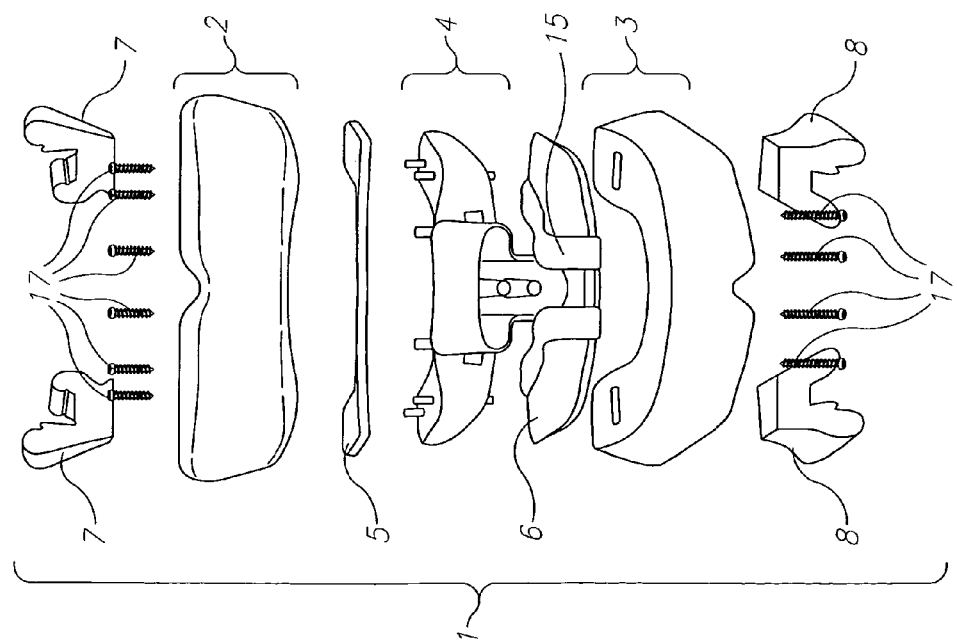
FIG. 5a is a vertical stack blow up front (buccal) view of one possible embodiment of components which comprise the double dental arch mouthpiece, according to some embodiments.

FIG. 5a is a vertical stack blow up front (buccal) view of one possible embodiment of components which comprise the double dental arch mouthpiece 1 of the present invention wherein are depicted the upper flexible dental arch well 2, the lower flexible dental arch well 3, the middle layer 4, the lower cover 5, the upper cover 6, the upper distal plug sealers 7, and the lower distal plug sealers 8. Also depicted are the heat transfer pins 17 and the printed circuit board(s) 15.

FIG. 5b is a vertical stack blow up back (lingual) view of FIG. 5a wherein are depicted the components which comprise the double dental arch mouthpiece 1 of the present invention wherein are depicted the upper flexible dental arch well 2, the lower flexible dental arch well 3, the middle layer 4, the lower cover 5, the upper cover 6, the upper distal plug sealers 7, and the lower distal plug sealers 8. Also depicted are the heat transfer pins 17. The printed circuit board 15 is not depicted in this illustration.

Figure 6A:
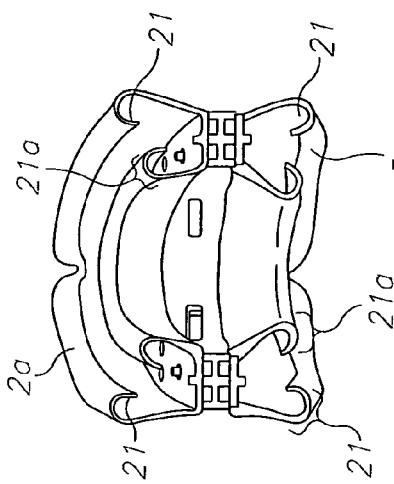
FIG. 6a is an inner (lingual) view of an example of a mouthpiece device, according to some embodiments.

FIG. 6a is an inner (lingual) view of an example of a mouthpiece device 1 wherein are depicted the upper dental arch well 2, the lower dental arch well 3, the upper distal plugs 7 and the lower distal plugs 8 as well as the air breathing vents 12.

Figure 6B:
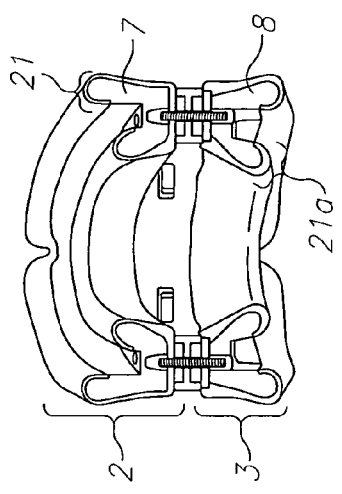
FIG. 6b illustrates a view of FIG. 6a where a distal cross-sectional vertical slice of the mouthpiece device has been taken, according to some embodiments.

FIG. 6b illustrates a view of FIG. 6a where a distal cross-sectional vertical slice of the mouthpiece device 1 has been taken, so as to remove the distal sealing walls 2d and 3d of the upper and lower dental arch wells respectively, so as to reveal the cross-sectional structure of the apron or curled cross sectional shape design 21 of the rim 2a of the dental arch upper well 2 and dental arch lower well 3. Additionally, the cross-sectional shape of the upper 7 and lower 8 distal plugs and their structural relation to the upper 2 and lower 3 wells respectively are revealed.

Figure 6C:
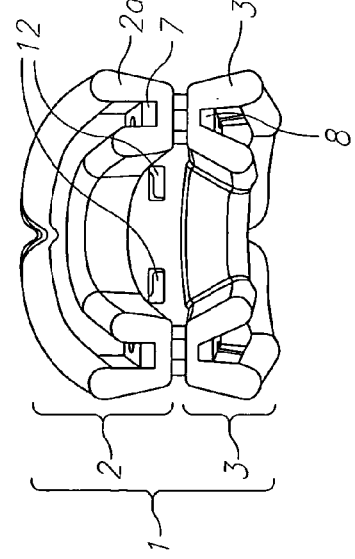
FIG. 6c depicts FIG. 6b wherein the upper 7 and lower 8 distal plugs have been removed, according to some embodiments.

FIG. 6c depicts FIG. 6b wherein the upper 7 and lower 8 distal plugs have been removed to better reveal the structural shape of the highly deformable outer curled apron 21 and inner curled apron 21a of the upper rim 2a and lower rim 3a of the dental arch wells.

Figure 6D:
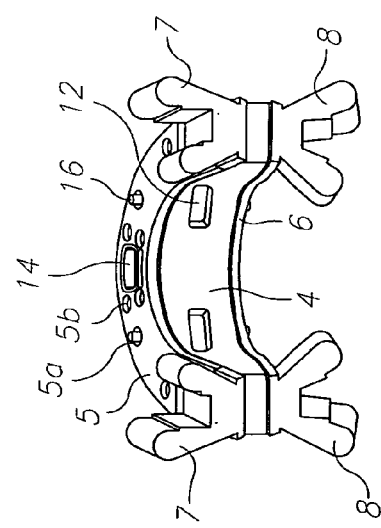
FIG. 6d is an inner (lingual) view of the middle layer, according to some embodiments.

FIG. 6d is an inner (lingual) view of the middle layer 4 with its upper 5 and lower 6 cover plate attached to which have been secured the upper 7 and lower 8 distal plug sealers respectively. Also depicted is the drain hole well 14 on the on the upper cover plate 5, the peg connectors 16 inserted through the upper cover plate holes 5a, and the upper cover plate hole 56b which accommodates the heat transfer pins head 17a (not depicted). Additionally, the illustration depicts the air breathing vents 12.

Figure 6E:
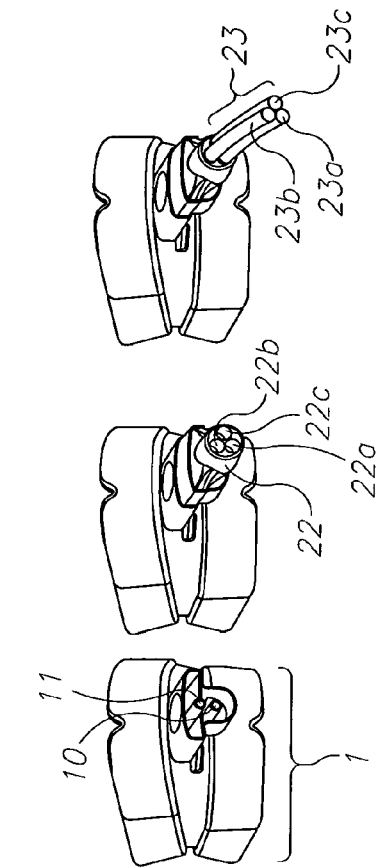
FIG. 6e is an angled front view of the mouthpiece device, according to some embodiments.

FIG. 6e is an angled front view of the mouthpiece device 1 wherein are depicted the mouthpiece in an array of three embodiments wherein the left most embodiment depicts the in-flow tube 10 and out-flow tube 11, the middle embodiment depicts the attachment of the quick-attach coupler 22, which integrates hole 22a which aligns with the in-flow tube 10, hole 22b which aligns with the out-flow tube 11, and hole 22c which aligns with the printed circuit board 15 (not depicted). Also depicted in the right most embodiment are the cable/tube bundle 23 which inserts into the quick-attach coupler 22 and which includes an out-flow tube 23b, an in-flow tube 23a, and a power cable 23c.

Figure 7:
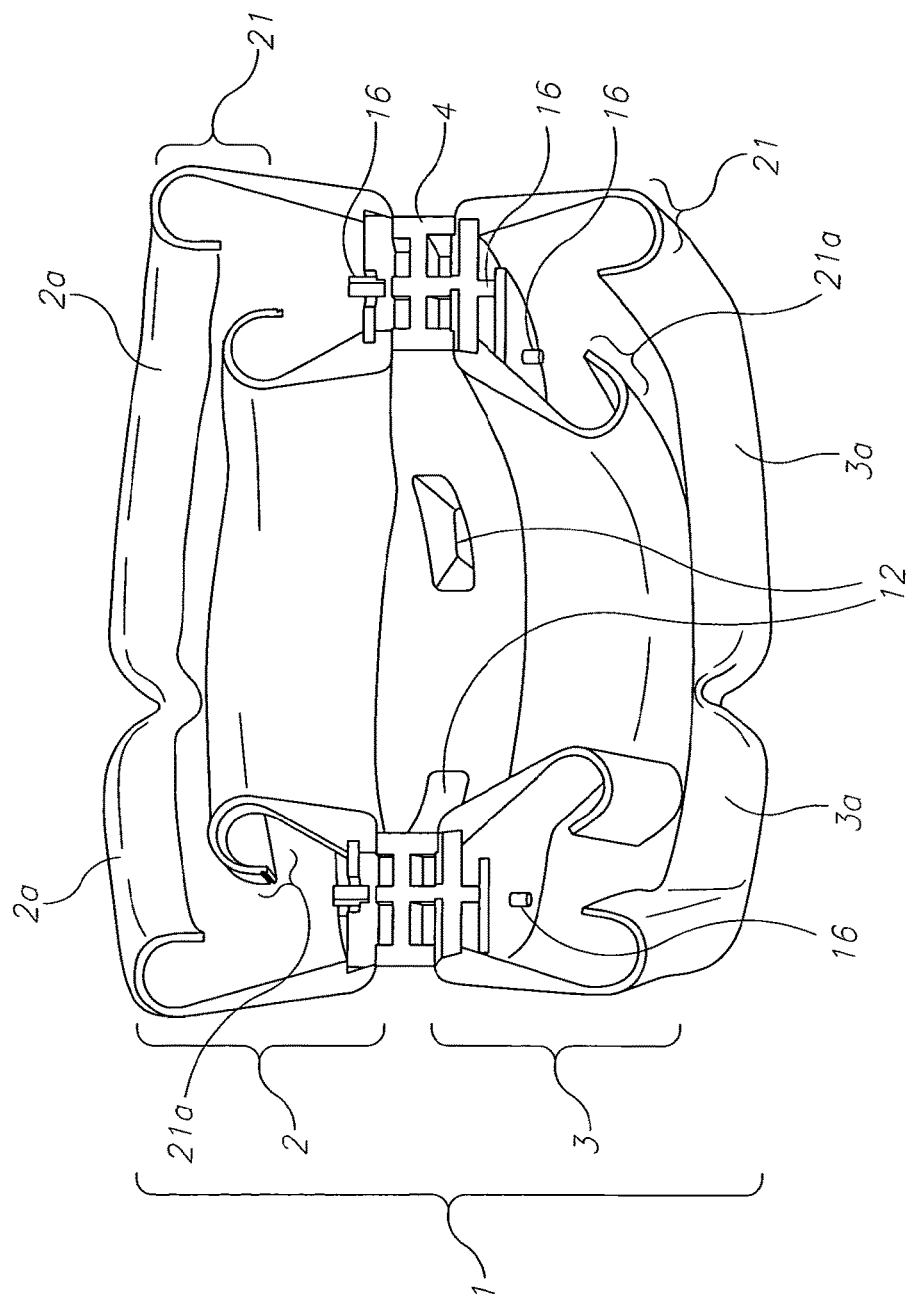
FIG. 7 is an inner (lingual) close up view of an example of a mouthpiece, according to some embodiments.

FIG. 7 is an inner (lingual) close up view of an example of a mouthpiece 1 wherein are depicted the upper arch well 2 with highly deformable outer apron 21 and inner apron 21a of its compressible rim 2a, the lower arch well 3 with its highly deformable outer apron 21 and inner apron 21a of its compressible rim 3a, the middle layer 4 with its air breathing vents 12, and the connector pins 16 which secure the upper 2 and lower 3 arch wells to the middle layer 4.

FIG. 8a is front (labial) view of an example of a mouthpiece 1 wherein are depicted the upper 2 and lower 3 arch wells in a see-through flexible material so as to reveal their covering respectively of the maxillary teeth 28 and maxillary alveolar gum ridges 26 of the upper jaw 24, and the mandibular teeth 27 and mandibular alveolar gum ridges 26a of the lower jaw 25. Also depicted is the middle layer 4 of the mouthpiece device 1, and the in-flow tube 10 and out-flow tube 11 of the mouthpiece device 1.

FIG. 8b is a close up inner side (facing the surface of the mouthpiece 1 not depicted) of the quick-attach coupler 22 wherein are depicted inner aspects of the holes 22a and 22b, and the printed circuit board connectors 22d.

FIG. 8c is a close up outer (facing away from the surface of the mouthpiece 1 not depicted) view of the quick attach connector 22, wherein are depicted the outer aspects of the holes 22a, 22b, 22c, and the thumb depression 22e on the top surface of the coupler 22.

FIG. 9a is an angled view of one side of an example of a pump mechanism assembly 30 wherein are depicted the flow control valve assembly 32 inserted into the control valve assembly frame 39, the flow control valve motor 33, the gear assembly 34 inserted into the gear assembly frame 42, the flexible pump membrane 36 inserted in the hole 38 of the flow control valve assembly 32, and the piston 41, attached to the drive shaft coupler 40. An example of a treatment material dispenser is depicted, for example fresh gel tube 32b, which connects to a fresh gel container 46 (not depicted) and the pump motor 31 inserted into the pump mechanism assembly floor 43.

FIG. 9b is an angled view of the opposite side of FIG. 9a wherein are depicted out-flow tube 32a, a treatment material tube 32b, the pump jumper tubes 32c and 32d, the pre-heating chamber 29 with its treatment material tube 29a, the heating transfer block 44 with its heating elements 45, the waste tube 32f and the rinse tube 32g, and the pump motor 31.

FIG. 9c is a top view of the pump mechanism assembly 30 wherein are depicted a see through view of the flow control valve assembly 32 which reveals the multi-position flow control valve 35 with its multiple holes 35a inside the flow control valve assembly 32. Also depicted is the pre-heating chamber 29 with its treatment material tube 29a attached to the multi-position flow control valve 35, the gear assembly 34, the flow control valve motor 33 and the multiple position holes 37 on the top surface of the drive shaft coupler 40.

FIG. 9d is a front view of the flow control valve assembly 32. The flow control valve assembly 32 includes an out-flow tube 32a and a treatment material tube 32b. The flow control valve assembly 32 includes pump jumper tubes 32c and 32d. The flow control valve assembly includes a pre-heating chamber flow attachment 32e for attachment to the pre-heating chamber 29 (not shown). The flow control valve assembly 32 further includes a waste tube 32f and a rinse tube 32g.

Figure 10:
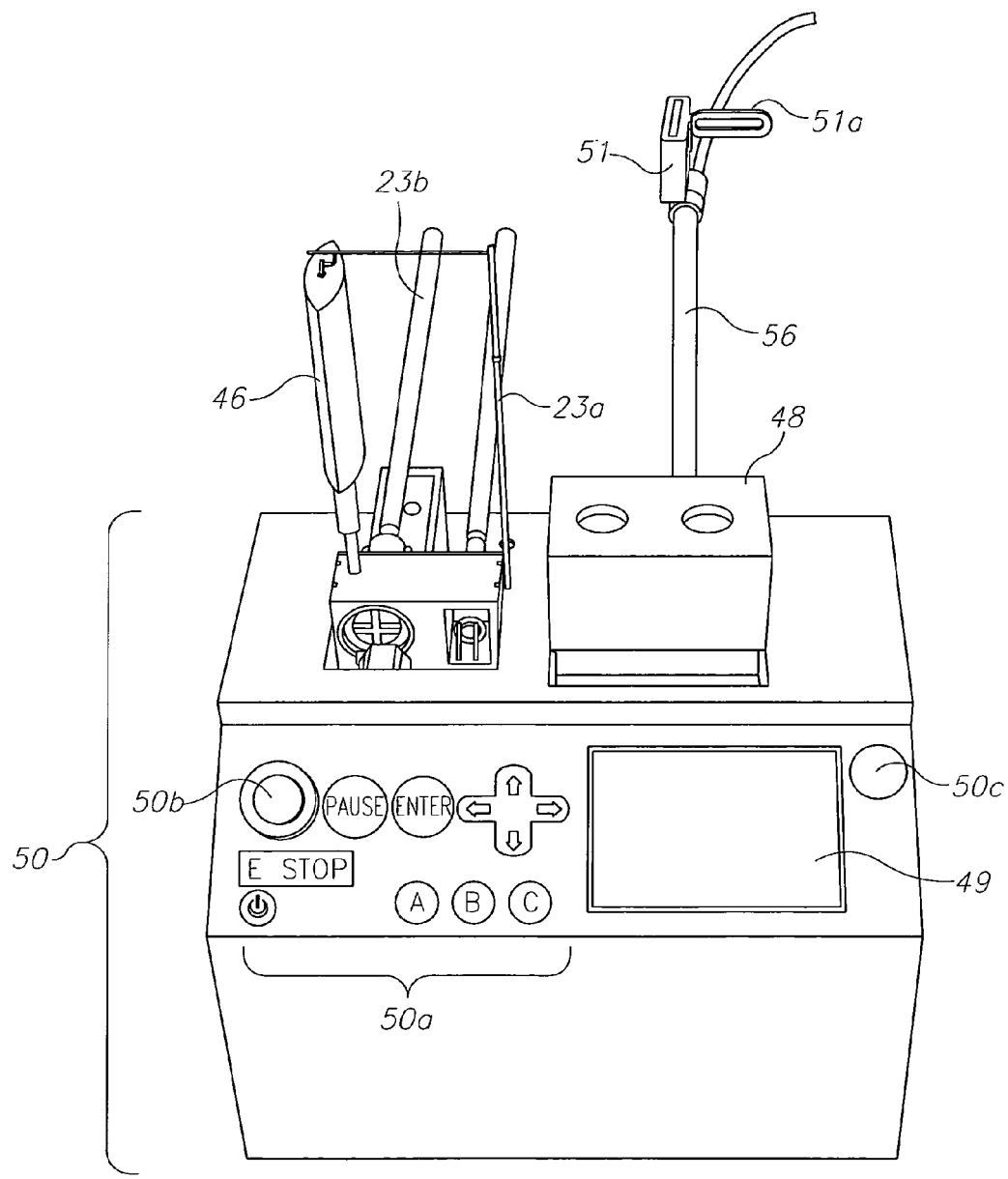
FIG. 10 is a top/front view of one possible embodiment of the control unit, according to some embodiments.

FIG. 10 is a top/front view of one possible embodiment of the control unit 50 wherein are depicted interactive screen 49, the interface buttons 50a, the emergency stop button 50b, the speaker 50c, the optionally rechargeable battery pack or power supply 48, a treatment material stand, for example gel container stand 47 (not indicated in drawing) to which is attached the gel container 46, the in-flow (to the mouthpiece device 1) tube 23a and the out-flow tube 23b, and the power cable 56 with attached quick-clip harness 51 with its clip 51a to organize the in-flow 23a and out-flow 23b tubes.

Figure 11:
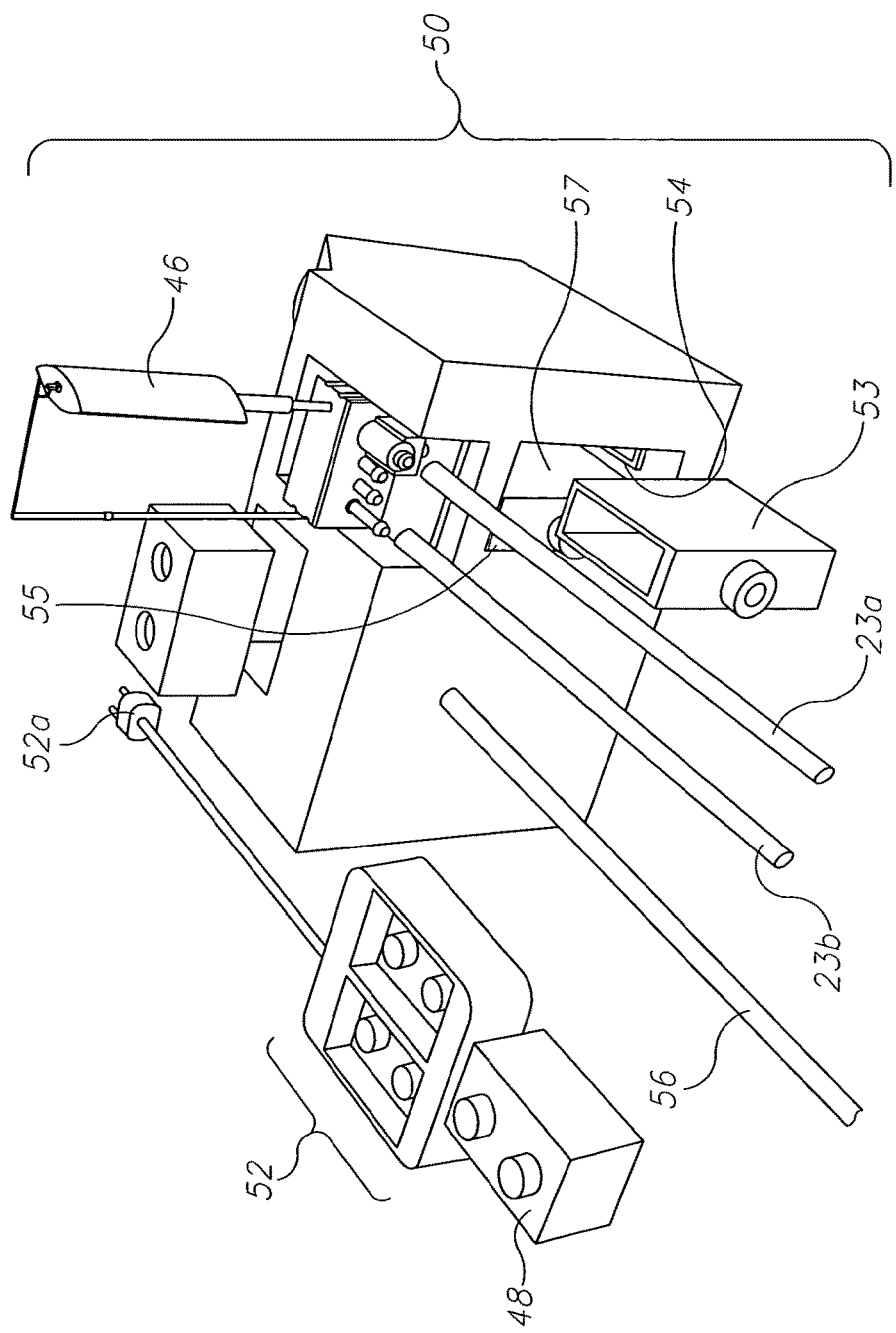
FIG. 11 is a top/back view of the control box 50 and the battery pack charger unit 52, according to some embodiments.

FIG. 11 is a top/back view of the control box 50 and the battery pack charger unit 52. Also depicted are the in-flow 23a and out-flow 23b tubes, the fresh water container 55 and waste water container 53 with its weight pressure sensor 54 on the floor of the water container compartment 57 of the control unit 50. Also depicted are the power cable 56, the battery pack 48, the battery charger plug 52a, and treatment material container 46.

Figure 12A:
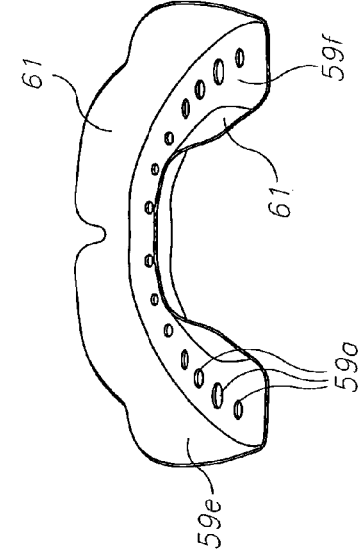
FIG. 12a is an outer surface (bottom) view of one possible embodiment of the upper gum guard, according to some embodiments.

FIG. 12a is an outer surface (bottom) view of one possible embodiment of the upper gum guard 59 wherein are depicted the outer floor 59d with its multiple teeth holes 59a of varying sized diameters and spacing, the outer side walls 59b, and the upper labial frenulum notch 59c.

Figure 12B:
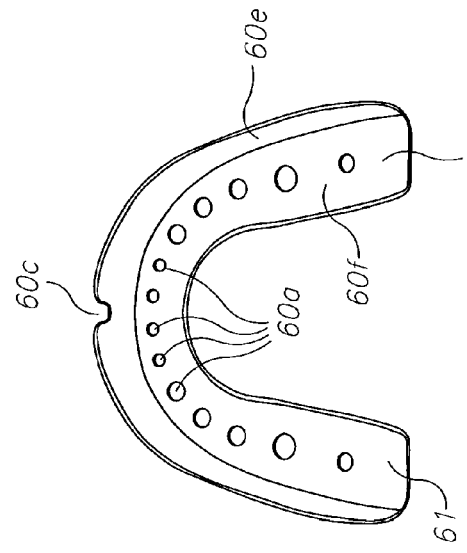
FIG. 12b is an inner surface (top) view of FIG. 12a, according to some embodiments.

FIG. 12b is an inner surface (top) view of FIG. 12a wherein are depicted the inner aspects of the teeth holes 59a, and the inner side wall 59e and inner floor 59f which, in some embodiments, may be coated with a treatment material neutralizing layer 61.

Figure 12C:
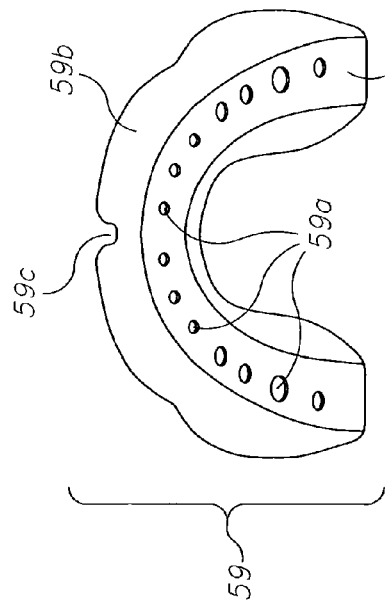
FIG. 12c is an outer surface (top) view of one possible embodiment of the lower gum guard, according to some embodiments.

FIG. 12c is an outer surface (top) view of one possible embodiment of the lower gum guard 60 wherein are depicted the outer floor 60d with its multiple teeth holes 60a of varying diameters and spacing, and the outer side walls 60b.

Figure 12D:
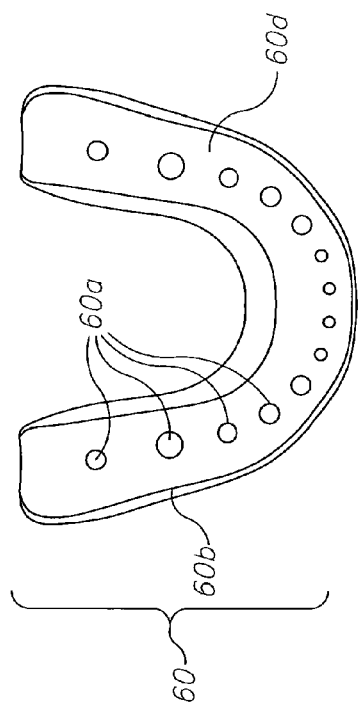
FIG. 12d is an inner (bottom) view of FIG. 12c, according to some embodiments.

FIG. 12d is an inner (bottom) view of FIG. 12c wherein are depicted the inner aspects of the teeth holes 60a, and the inner side walls 60e and inner floor 60f which may be coated with a treatment material neutralizing layer 61. Also depicted is the lower labial frenulum notch 60c.

FIG. 13a is a front vertically stacked view of the upper gum guard 59 and the lower gum guard 60.

FIG. 13b is a front view of the upper jaw 24 wherein are depicted a see-through version of the upper gum guard which has been pulled over the maxillary teeth 28 and is sitting on the upper alveolar gum ridges 26 and the lower jaw 25 with a see-through version of the lower gum guard 60 which has been pulled over the mandibular teeth 27 and is sitting on the lower alveolar gum ridges 26a.

FIG. 13c is a front view of an example of a mouthpiece device 1 inserted between the upper 24 and lower 25 jaws respectively, and wherein are depicted the upper arch well 2 and lower arch well 3 of the mouthpiece 1. Also depicted are the upper gum guard 59 and lower gum guard 60 onto which is seated the mouthpiece 1. Additionally, the illustration depicts the mouthpiece handle 9 to which is attached the quick-attach coupler 22 with its cable/tube bundle 23 attached to it. An upper gum guard may cover at least a portion of an upper alveolar ridge, such as illustrated in FIGS. 12a, 12b, 12c, 13a, 13b, and 13c. Similarly, a lower gum guard may cover at least a portion of a lower alveolar ridge. The number of holes in a gum guard may be sufficient so that there is a hole for each tooth in the corresponding alveolar ridge.

Figure 14:
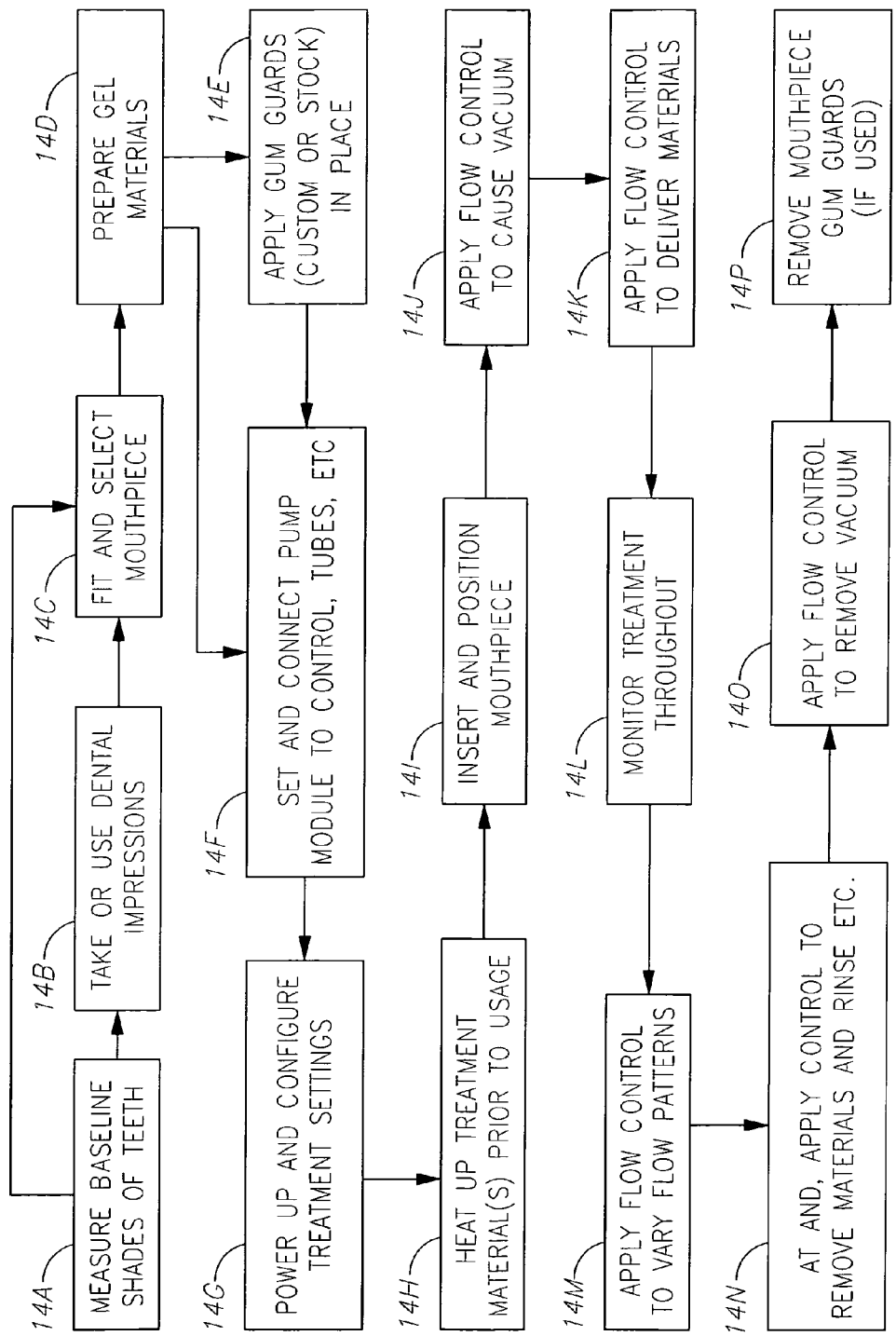
FIG. 14 is a flow chart describing an example of a process of implementing a tooth whitening treatment using a mouthpiece and associated components as described herein, according to some embodiments.

FIG. 14 is a flow chart describing an example of a process of implementing a tooth whitening treatment using a mouthpiece and associated components as described herein, according to some embodiments. At step 14a, at the initial visit the dental practitioner or dental staff determine and document the current (baseline) shades of the teeth to be whitened. This may be accomplished by using the optional shade guide comparator sensor device that may be provided with the control unit, or an alternative shade guide comparator. If needed, at step 14B, initial dental impressions of the arch or arches to be treated may be taken and dental stone models of the arches are poured as is well known in the field. These models may then be used to fabricate a custom made disposable gum protector as has been described above. Alternatively, various stock sized gum protector/guards may be used in conjunction with matching stock sizes of the mouthpiece device without the need to take dental impressions or the fabrication of dental stone models. At step 14C the customized or appropriate stock mouthpiece is provided, fitted, and selected based on good fitting to the patient's mouth.

At the treatment visit, at step 14D, the system is to be calibrated and treatment materials prepared. For example, a fresh gel container may be connected to the disposable pump assembly that has been inserted into the control unit and fresh water may be filled into the refillable fresh water container. At step 14E disposable gum protector/guards may be applied and fitted to the gums and or alveolar gum ridges of the upper and lowers jaws and adapted to the teeth to provide a sealed barrier between the teeth and the soft tissues immediately surrounding the teeth. If a milder concentration of treatment material is to be used then the gum protector/guards may not be required. At step 14F, the relevant tubes are connected to the treatment material container and the pump mechanism. The disposable tubing is now also connected to the mouthpiece device and may include a harness, clip, or other attachment elements to hold the tubes in a specific orientation and position in relation to the mouthpiece device and the patient. At step 14G the control unit is powered up and the treatment settings configured and may include, for example, configuring a customized treatment plan or session for a patient, in accordance with their particular whitening needs or expectations, comfort zone, and health condition.

At step 14H, the treatment material(s) may be pre-heated in the heating chamber of the pump mechanism. At step 14I the mouthpiece is inserted into the mouth and the patient may be instructed to close and bite down into the mouthpiece etc. At step 14J the control unit may apply flow control to cause a vacuum around the alveolar ridges. For example, the control unit may activate the motor which then rotates the flow control valve to the vacuum position to activate the pump to suck out the air contained between the mouthpiece and the alveolar ridges of the upper and lower jaws on which it rests. This negative pressure inside the mouthpiece creates a vacuum seal of the mouthpiece to these ridges as the thin flexible soft rim or apron of the rims of the mouthpiece are sucked tightly up against and conform to the gums covering the buccal and lingual plates of alveolar ridges of the upper and lower jaws. This vacuum seal may be monitored by a pressure sensor throughout the treatment. In some embodiments, if the vacuum seal is compromised, the control unit may warn the user of the loss of vacuum integrity.

At step 14K, the control unit may apply flow control to enable delivery of treatment materials. For example, the control unit may activate the motor which then rotates the flow control valve to the treatment materials delivery position and then also activates the pump component to deliver a selected amount of the treatment material that has been pre-heated to a set temperature by the heating element contained in the control unit which is in contact with a heating chamber element of the pump component optionally at a controlled rate to the mouthpiece device. In some embodiments, various other changes may be executed during the treatment, such as heating up of treatment materials inside the mouthpiece, or otherwise managing the timing, materials, temperatures, lighting etc. in the treatment environment.

At step 14L the control unit continues to monitor the treatment settings throughout the treatment. For example, the control unit may monitor the various pre-configured settings of flow rates, temperature of the individual heating elements in the mouthpiece, material compositions, exposure intervals etc. For example, the pump component may pump pre-heated whitening gel into the internal well(s) of the mouthpiece device and the flow rate and total amount of gel dispensed and delivered may be controlled by pressure sensor(s) or other sensors located throughout the system and the microprocessor controller of the control unit. In some cases, for example, the microprocessor may further control the various temperature outputs of each of the multiple heating elements in the mouthpiece, during the treatment process.

In some embodiments, a pressure sensor may be incorporated in the pump mechanism to monitor the internal pressure inside the mouthpiece device throughout the treatment. In one example, increasing pressure inside the mouthpiece signifies degradation of the vacuum seal integrity and increase the potential risk that treatment materials will leak out of the mouthpiece and into the patient's mouth or alternatively, allow saliva to enter into the mouthpiece. Both of these possibilities are undesirable.

Chemically active treatment materials, such as whitening agents, may release, for example, oxygen during its oxidation/whitening reaction. This release of free oxygen from a gel may increase the internal pressure inside the mouthpiece device. In some embodiments, if the internal pressure (monitored by the pressure sensor and the microprocessor) reaches a critically high value, the patient may be told to bite down harder on the mouthpiece and the system will automatically begin evacuating the treatment materials contained within the mouthpiece and either pump in water to rinse the teeth or alternatively, pump in new treatment material. Alternatively, removing overactive treatment material present in the mouthpiece with fresh treatment material(s) may help in decreasing the internal pressure inside the mouthpiece and so allow for continuing the treatment without the need to rinse the teeth.

At step 14M, the microprocessor may activate flow controls to vary flow patterns, as may be necessary. For example, the motor may be activated to rotate the control flow valve to the position that allows for a "closed-circuit" flow of the treatment materials already delivered into the mouthpiece to circulate within the full upper and lower arch form wells of the mouthpiece, either in a steady flow pattern or in a sporadic pulsatile manner. In some implementations, the direction of flow within the mouthpiece may be alternated as well, creating a further dynamically turbulent flow of the treatment materials similar to the convection flow of a gas or liquid. In some embodiments, additional treatment modalities may be applied during the treatment as may be necessary, whether by manual action by a practitioner or assistant, and/or whether via programming of the control unit. For example, several applications of fresh gel may be required for each whitening treatment in the same patient as the quantity of gel material used to fill the mouthpiece device to a specific level within each well has a limited chemical reaction potential to release the oxygen free radical and so effect a whitening of the teeth.

In further embodiments, the microprocessor of the control unit may be set to monitor substantially in real time the treatment time duration and/or temperature settings for each zone or area of the mouthpiece device, the patient situation etc. optionally throughout the treatment. In some embodiments, a built in screen in the control unit displays this data to the user or practitioner throughout the whitening procedure. In some embodiments alerts may be generated as may be necessary, to warn a practitioner of any problems, dangers, complications etc. For example, the control unit may alert the operator via buzzer sounds, voice activation messages, and or lighted indicators when each gel application treatment is complete or warn about gel volumes, gel temperatures, and vacuum pressure values etc. in the mouthpiece that are not desirable.

At the end of the treatment, at step 14N, the control unit may apply flow control to remove treatment materials and/or rinse out treatment materials. For example, to facilitate the removal of the spent whitening gel (chemically less active or inactive) from the well(s) of the mouthpiece device, the microprocessor may activate the motor which then rotates the flow control valve to the position which allows the pump mechanism of the system (which has also been activated by the microprocessor) or a separate suction device common to a dental operatory which has been attached to the tray device, (such as may be used in case of catastrophic failure of the pump or control system or both) to substantially remove the spent or remaining gel material from the mouthpiece device. Alternatively, spent chemically inactive treatment materials can be simply replaced by pumping new treatment materials into the mouthpiece. In some embodiments, to remove any residual spent whitening gel from the tooth surfaces and the inner surfaces of the mouthpiece, fresh water may be pumped into the treatment area, for example, from a removable container of fresh water included and connected to the pump and flow control valve unit. The water may be delivered by these to the inside of the mouthpiece via the same flexible tubing and can be used to rinse or flush the residual spent treatment materials out to a separate disposal container. In one example, a sensor such as a simple weight sensor or other type sensor may be incorporated beneath or adjacent to the water disposal container to monitor the amount of water used in each rinse/flush cycle.

At step 14O, the flow control valve may be activated to release the vacuum seal of the mouthpiece to the alveolar gum ridges and teeth, for example, by pumping air into the mouthpiece.

At Step 14P, the mouthpiece and gum guards (if used) are removed from the patient's mouth and the optional shade comparator device may be used to record the whitening results obtained.

The above described features of the system allow for the easy and rapid removal of treatment material and from the mouthpiece device so that upon removing the mouthpiece device from the patient, there remains little of the spent treatment material both in the mouthpiece device itself and on the enamel surfaces of the treated teeth. This simplifies the operator's task of removing any partially or completely spent treatment material from the patient's mouth. In some implementations, the controlled removal of the spent treatment materials may be automated by the control unit at the end of a set period of time or manually initiated by the operator's pressing a button which activates the removal/suctioning of the material at any time during the treatment.

Alternatively, as mentioned above, spent treatment materials may be rapidly removed (suctioned) via the evacuation system of the standard dental operatory unit.

In some embodiments, several applications (of a volume of gel required to fill the mouthpiece) of fresh treatment materials may be so applied and removed until the operator and patient are satisfied with the whitening results achieved. Of course, any combination of the above steps may be implemented. Further, other steps or series of steps may be used.

In the respective embodiments of the present invention, the above described design elements allow for the rapid, intense and controlled whitening of a dental arch or arches of both the anterior and posterior teeth simultaneously and the whitening of both the outer (buccal), inner (lingual) and occlusal (top/biting) surfaces of both the anterior and posterior teeth. These embodiments further enable effectively protecting the patient's soft tissues from the caustic effects of the various concentrations of whitening agents applied to the teeth, whilst optionally maintaining and monitoring in real time the safety, progress and/or comfort of the patient throughout the treatment.

According to some embodiments, the present invention's dental arch mouthpiece design allows for a novel "compression" whitening technique (based on its novel vacuum seal integrity of the mouthpiece in the mouth) which potentiates the oxidation (whitening) effect by forcing oxygen ions into the enamel surfaces of the teeth. As mentioned above, this compression technique also protects whitening gel from any deactivation by the salivary peroxidase enzyme and so further enhances the whitening effect of a given quantity of gel delivered to the inside of the mouthpiece device of the present invention.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

The principles and operation of the device, and method according to the present invention may be better understood with reference to the drawings, and the following description, it being understood that these drawings are given for illustrative purposes only and are not meant to be limiting, wherein:

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are not intended to cover all such modifications and changes as fall within the true spirit of the invention.

What is claimed is:

1. A device comprising:
an arch shaped mouthpiece having opposing left and right ends configured to fit over dental arches for implementing a dental treatment, wherein the mouthpiece includes:
  i. one or more stock dental covers suitable for forming one or more treatment cavities having a vacuum seal, wherein each of the dental covers is adapted to form a treatment cavity over the upper teeth and surrounding gums and/or a treatment cavity over the lower teeth and surrounding gums, and wherein a dental cover fluid seal is formed using a continuous sealing mechanism that includes a sealing rim formed of compressible material for sealing along a length of the dental covers, and at least one pair of sealing plugs for sealing the opposing left and right rear openings of each of the one or more dental covers, whereby the sealing rim and at least one pair of sealing plugs sufficiently seals each of the treatment cavities to enable the reduction of pressure in the dental treatment cavity below ambient pressure, to selectively enable material flow into and out of each of the dental treatment cavities; and
  ii. one or more treatment supply portions wherein each of the treatment supply portions has one or more flow channels in fluid communication with the one or more treatment cavities so that the one or more treatment supply portions can deliver and/or remove one or more treatment fluids from the one or more treatment cavities;

wherein each of the sealing plugs has variable dimensions for providing optimal sealing despite variability between different dental arch dimensions and/or different terminal teeth positions.

2. The device of claim 1, wherein each of the at least one pair of sealing plugs are made of a material that is sufficiently deformable so that the plug intimately contours to the tooth anatomy of one or more of the rear teeth despite variability between different dental arch dimensions and/or different terminal teeth dimensions.

3. The device of claim 1, wherein the one or more treatment cavities includes one or more controllable heating elements for heating the one or more treatment fluids.

4. The device of claim 1, wherein the device includes
one or more inflow tubes connected to a handle integrated into the treatment supply portions suitable for flowing one or more treatment materials into the treatment supply portion(s); and
one or more outflow tubes connected to the handle for flowing one or more treatment materials out of the treatment supply portion(s).

5. The device of claim 1, wherein the device includes two of the dental covers for covering the upper teeth and surrounding gums and the lower teeth and surrounding gums; at least one treatment supply portion interposed between the two dental covers to enable the upper teeth and surrounding gums and lower teeth and surrounding gums to be treated simultaneously; wherein the device includes one or more breathing vents for providing an air passage into and out of the mouth during a dental treatment.

6. The device of claim 1, wherein the mouthpiece includes: one or more delivery channels for flowing the one or more treatment fluids from the treatment supply portion(s) to the one or more treatment cavities, and one or more drainage channels for flowing the one or more treatment fluids from the one or more treatment cavities to the treatment supply portion(s).

7. A system comprising: the device of claim 1, wherein the vacuum seal is formed via the treatment supply portion(s), by reducing the pressure in the one or more dental treatment cavities below ambient pressure for conforming the one or more dental covers onto the gum ridges of the upper and/or lower teeth.

8. The system of claim 7, wherein the system includes:
i. a pumping system for pumping one or more treatment materials into the mouthpiece;
ii. a multi-position flow control module; and
iii. a control unit for automating the dental treatment.

9. A system comprising:
i. the device of claim 1, and
ii. a dental gum guard component having a treatment layer on its inner surfaces for neutralizing a treatment material of the one or more treatment fluids.

10. A method for executing a dental treatment, comprising:
i. positioning the device of claim 1 including the mouthpiece having one or more dental covers over upper and/or lower teeth and surrounding gums;
ii. applying a vacuum seal to the one or more dental covers for generating a pressure below ambient pressure in the one or more treatment cavities around the teeth; and
iii. flowing one or more treatment materials into the one or more sealed treatment cavities; and
iv. flowing the one or more treatment materials out of the one or more sealed treatment cavities.

11. The method of claim 10, wherein the process includes one or any combination of the following steps:
i. setting up a pump module to connect to a mouthpiece designed for a treatment;
ii. configuring treatment settings on a control device coupled to the pump module;
iii. applying flow control to cause a vacuum seal between the mouthpiece and the patient's gum ridge anatomy; and
iv. applying flow control to automatically manage delivery of materials in accordance with said treatment settings, and/or using a flow control module to remove treatment materials from said mouthpiece.

12. The method of claim 10, wherein the method includes one or any combination of the following:
i) a step of applying flow control to change flow patterns during a treatment, in order to optimize conformance to a treatment plan;
ii) a step of monitoring the treatment to track conformance to a treatment plan; or
iii) a step of monitoring the treatment to identify problems during a treatment.

13. The device of claim 1, wherein each of the one or more stock dental covers incorporates a deformable rim to conform to a gum ridge.

14. The device of claim 1, wherein the device is shaped to mirror a hinge axis angle to facilitate natural jaw movement.

15. A kit comprising the device of claim 1 and two or more dental gum guards including a first dental gum guard and a second dental gum guard having a different number and/or a different dimensions of the pre-configured holes.

16. A system comprising:
a. a deformable dental gum guard for selectively covering a gum ridge wherein the crown portions of the teeth of said gum ridge are not covered; and
b. a dental treatment device; comprising an arch shaped mouthpiece having opposing left and right ends for configured to fit over dental arches for implementing a dental treatment, wherein the mouthpiece includes:
i. one or more stock dental covers suitable for forming one or more treatment cavities having a vacuum seal, wherein each of the dental covers is adapted to form a treatment cavity over the upper teeth and surrounding gums and/or a treatment cavity over the lower teeth and surrounding gums, and wherein a dental cover fluid seal is formed using a continuous sealing mechanism that includes a sealing rim formed of compressible material for sealing along a length of the dental covers, and at least one pair of sealing plugs for sealing the opposing left and right rear openings of each of the one or more dental covers, whereby the sealing rim and at least one pair of sealing plugs sufficiently seals each of the treatment cavities to enable the reduction of pressure in the dental treatment cavity below ambient pressure, to selectively enable material flow into and out of each of the dental treatment cavities; and
ii. one or more treatment supply portions wherein each of the treatment supply portions has one or more flow channels in fluid communication with the one or more treatment cavities so that the one or more treatment supply portions can deliver and/or remove one or more treatment fluids from the one or more treatment cavities;

wherein the gum guard and the at least one pair of sealing plugs seals a gap between at least a portion of the device and the gum ridge over which it lies;

the gum guard contacts and deforms against at least a portion of the gum ridge for forming an intimate contact with the gum, and wherein the placement of the one or more dental covers in a patient's mouth over a plurality of teeth and gum ridge acts in conjunction with the gum guard and the at least one pair of sealing plugs for substantially defining a seal at the distal tooth, so that a fluid can be introduced, removed, or both from the one or more treatment cavities while maintaining a vacuum seal in the one or more treatment cavities.

17. The system of claim 16, wherein the dental gum guard has an arch-shaped, elastomeric drape designed to conform substantially to any gum ridge anatomy, and having a plurality of pre-configured holes including holes of different initial diameters for customized insertion of the dental gum guard over a gum with crown portions of teeth penetrating through the holes, wherein the dental gum guard acts to provide a dry field around the crown portion of each tooth.

18. The dental gum guard of claim 17, wherein the dental gum guard includes an inner surface having a gum treatment layer containing one or more therapeutic treatment materials for the delivery of the one or more therapeutic treatment materials to the gums.

19. The system of claim 17, wherein the plurality of holes of the gum guard includes a hole for each tooth in the alveolar ridge.

20. The system of claim 17, wherein the holes of the gum guard are perforated holes.

21. The system of claim 17, wherein the holes of the gum guard are cut-out holes.

22. The system of claim 17, wherein the elastomeric drape of the gum guard is flexible and fits snuggly against the alveolar ridge.

23. A treatment system comprising:

a dental treatment device including an arch shaped mouthpiece having opposing left and right ends configured to fit over dental arches for implementing a dental treatment; and one or more dental gum guards;

wherein the mouthpiece includes:
  i. one or more stock dental covers suitable for forming one or more treatment cavities having a vacuum seal, wherein each of the dental covers is adapted to form a treatment cavity over the upper teeth and surrounding gums and/or a treatment cavity over the lower teeth and surrounding gums, and wherein a dental cover fluid seal is formed using a continuous sealing mechanism that includes a sealing rim formed of compressible material for sealing along a length of the dental covers, and at least one pair of sealing plugs for sealing the opposing left and right rear openings of each of the one or more dental covers, whereby the sealing rim and at least one pair of sealing plugs sufficiently seals each of the treatment cavities to enable the reduction of pressure in the dental treatment cavity below ambient pressure, to selectively enable material flow into and out of each of the dental treatment cavities; and
  ii. one or more treatment supply portions wherein each of the treatment supply portions has one or more flow channels in fluid communication with the one or more treatment cavities so that the one or more treatment supply portions can deliver and/or remove one or more treatment fluids from the one or more treatment cavities; and wherein the one or more dental gum guard component(s) each includes one or more arch-shaped, elastomeric drape(s) designed to conform substantially to any gum ridge anatomy, and a plurality of pre-configured cut-out holes for customized insertion over and through erupted teeth which provide protection of the gums from the treatment materials contained within the one or more treatment cavities, when the dental treatment device is placed over the one or more dental gum guard component(s).

24. A method for executing a dental treatment comprising:
i. positioning a mouthpiece including one or more dental covers over upper and/or lower teeth and surrounding gums;
ii. applying a vacuum seal to the one or more dental covers for generating a pressure below ambient pressure in the one or more treatment cavities around the teeth; and
iii. flowing one or more treatment materials into the one or more sealed treatment cavities; and
iv. flowing the one or more treatment materials out of the one or more sealed treatment cavities;

wherein prior to positioning of the mouthpiece, the method includes inserting one or more gum guards, the gum guard comprising an arch-shaped, elastomeric drape designed to conform substantially to any gum ridge anatomy, and having a plurality of pre-configured cut-out holes for customized insertion over and through erupted teeth, which provides protection of the gums exposed within the device from the treatment materials contained within the one or more treatment cavities;

wherein the method includes placing the mouthpiece over the one or more gum guards; and the step of applying a vacuum seal to the one or more dental covers generates a fluid seal around the teeth and the dental anatomy covered by the one or more gum guards.

25. A device comprising:

an arch shaped mouthpiece having opposing left and right ends for configured to fit over dental arches for implementing a dental treatment, wherein the mouthpiece includes:
  i. one or more stock dental covers suitable for forming one or more treatment cavities having a vacuum seal, wherein each of the dental covers is adapted to form a treatment cavity over the upper teeth and surrounding gums and/or a treatment cavity over the lower teeth and surrounding gums, and wherein a dental cover fluid seal is formed using a continuous sealing mechanism that includes a sealing rim formed of compressible material for sealing along a length of the dental covers, and at least one pair of sealing plugs for sealing the opposing left and right rear openings of each of the one or more dental covers, whereby the sealing rim and at least one pair of sealing plugs sufficiently seals each of the treatment cavities to enable the reduction of pressure in the dental treatment cavity below ambient pressure, to selectively enable material flow into and out of each of the dental treatment cavities; and
  ii. one or more treatment supply portions wherein each of the treatment supply portions has one or more flow channels in fluid communication with the one or more treatment cavities so that the one or more treatment supply portions can deliver and/or remove one or more treatment fluids from the one or more treatment cavities;

wherein each of the treatment cavities is at least partially defined by a pair of drapable aprons each having a J-shaped cross-section; each pair of drapable aprons includes a front apron for overlaying a front surface of the teeth and a rear apron for overlaying a rear surface of the teeth; and the front apron has a generally upright section connected to a generally curved section, wherein the generally upright section has a wall thickness greater than a wall thickness of the generally curved section.

26. The device of claim 25, wherein each of the sealing plugs are attachable to the rear opening(s) and are interchangeable so that each of the plugs have variable dimensions for providing optimal sealing despite variability between different dental arch dimensions and/or different terminal teeth positions.

\* \* \* \* \*